US006649346B2

(12) United States Patent
Südhof et al.

(10) Patent No.: US 6,649,346 B2
(45) Date of Patent: Nov. 18, 2003

(54) METHODS OF IDENTIFYING AGENTS THAT AFFECT CLEAVAGE OF AMYLOID-β PRECURSOR PROTEIN

(75) Inventors: Thomas C. Südhof, Dallas, TX (US); Xinwei Cao, Dallas, TX (US)

(73) Assignee: Board of Regents, The University of Texas, Austin, TX (US)

( * ) Notice: Subject to any disclaimer, the term of this patent is extended or adjusted under 35 U.S.C. 154(b) by 0 days.

(21) Appl. No.: 09/821,861

(22) Filed: Mar. 30, 2001

(65) Prior Publication Data

US 2003/0022171 A1 Jan. 30, 2003

(51) Int. Cl.[7] ............... C12Q 1/68; C12P 19/34; C12N 15/00; C12N 5/02

(52) U.S. Cl. ............... 435/6; 435/91.1; 435/325; 435/320.1

(58) Field of Search ............... 435/6, 91.1, 320.1, 435/325

(56) References Cited

U.S. PATENT DOCUMENTS

| | | | |
|---|---|---|---|
| 5,928,882 A | 7/1999 | Sabo et al. ............... | 435/7.21 |
| 5,972,634 A | 10/1999 | Tanzi et al. ............... | 435/7.94 |
| 5,981,208 A | 11/1999 | Tamburini et al. ............... | 435/23 |
| 6,020,143 A | 2/2000 | St. George-Hyslop et al. ............... | 435/7.1 |
| 6,043,224 A | 3/2000 | Lee et al. | |
| 6,083,904 A | 7/2000 | Artavanis-Tsakonas ......... | 514/2 |
| 6,114,133 A | 9/2000 | Seubert et al. ............... | 435/7.94 |
| ,034,884 A1 | 10/2001 | Peraus ............... | 800/3 |
| ,061,553 A1 | 5/2002 | Maury et al. ............... | 435/69.1 |

FOREIGN PATENT DOCUMENTS

| | | | | |
|---|---|---|---|---|
| DE | WO 00/34511 | * | 6/2000 | ............ C12Q/1/68 |
| WO | 9904746 | | 2/1999 | |
| WO | 0002897 | | 1/2000 | |

OTHER PUBLICATIONS

Duilio et al., 1991, Nucleic Acids Research, vol. 19, No. 19, pp. 5269–5274.*

Kidd et al., "Ligand–induced cleavage and regulation of nuclear entry of Notch in *Drosophila melanogaster* embryos", Genes & Development 12:3728–3740, 1998.

Steiner et al., "A Loss of Function Mutuation of Presenilin–2 Interferes with Amyloid β–Peptide Production and Notch Signaling", Journal of Biological Chemistry, 274:28669–28673, 1999.

Octave et al., "The Role of Presenilin–1 in the γ–Secretase Cleavage of the Amyloid Precursor Protein of Alzheimer's Disease", Journal of Biological Chemistry, 275:1525–1528, 2000.

Baek SH, Ohgi KA, Rose DW, Koo EH, Glass CK, Rosenfeld MG. Exchange of N–CoR corepressor and Tip60 coactivator complexes links gene expression by NF–kappaB and beta–amyloid precursor protein. Cell. Jul. 12, 2002;110(1): 55–67.

Kinoshita A, Whelan CM, Berezovska O, Hyman BT. The gamma secretase–generated carboxyl–terminal domain of the amyloid precursor protein induces apoptosis via Tip60 in H4 cells. J Biol Chem. Aug. 9, 2002;277(32):28530–28536.

Bruni P, Minopoli G, Zambrano N, Hansen U, Russo T. A possible function of the APP–Fe65 Complex in gene regulation. Abst Soc Neurosci 2001;27:2084.

Cao X, Sudhof TC. A transcriptionally [correction of transcriptively] active complex of APP with Fe65 and histone acetyltransferase Tip60. Science Jul. 6, 2001;293(5527): 115–120.

Cupers P, Orlans I, Craessaerts K, Annaert W, De Strooper B. The amyloid precursor protein (APP)–cytoplasmic fragment generated by gamma–secretase is rapidly degraded but distrubutes partially in a nuclear fraction of neurones in culture. J Neurochem Sep. 2001;78(5):1168–1178.

Gao Y. Pimplikar SW. The gamma –secretase–cleaved C–terminal fragment of amyloid precursor protein mediates signaling to the nucleus. Proc Natl Acad Sci USA Dec. 18, 2001;98(26):14979–14984.

Kimberly WT, Zheng JB, Guenette SY, Selkoe DJ. The intracellular domain of the beta–amyloid precursor protein is stabilized by Fe65 and translocates to the nucleus in a notch–like manner. J Biol Chem Oct. 26, 2001;276(43): 40288–40292.

Kimberly WT, Zheng JG, Guenette SY, Selkoe DJ. The amyloid precursor protein P6 C–terminal fragment localizes to the nucleus in COS cells. Abst Soc Neurosci 2001;27:25.

Sastre M, Steiner H, Fuchs K, Capell A, Multhaup G, Condron MM, Teplow DB, Haass C. Presenilin–dependent gamma–secretase processing of beta–amyloid precursor protein at a site corresponding to the S3 cleavage of Notch. EMBO Rep Sep. 2001;2(9):835–841.

Sudol M, Silwa K, Russo T. Functions of WW domains in the nucleus. FEBS Lett 2001;490:190–195.

Wolfe MS, Haass C. The role of presenilins in gamma–secretase activity. J Biol Chem Feb. 23, 2001;276(8): 5413–5416.

Yu C, Kim SH, Ikeuchi T, Xu H, Gasparini L, Wang R, Sisodia SS. Characterization of a presenilin–mediated amyloid precursor protein carboxy–terminal fragment gamma. Evidence for distinct mechanisms involved in gamma – secretase processing of the APP and Notch1 transmembrane domains. J Biol Chem Nov. 23, 2001;276(47):43756–43760.

(List continued on next page.)

*Primary Examiner*—Yvonne Eyler
*Assistant Examiner*—Olga N. Chernyshev
(74) *Attorney, Agent, or Firm*—Baker Botts L.L.P.

(57) ABSTRACT

The present invention provides methods of identifying agents that affect the cleavage of amyloid-β precursor protein (APP) and related vectors, cells and kits, as well as agents identified by the method.

4 Claims, 8 Drawing Sheets

OTHER PUBLICATIONS

Brown MS, Ye J, Rawson RB, Goldstein JL. Regulated intramembrane proteolysis: a control mechanism conserved from bacteria to humans. Cell Feb. 18, 2000;100(4):391–398.

Esler WP, Kimberly WT, Ostaszewski BL, Diehl TS, Moore CL, Tsai JY, Rahmati T, Xia W, Selkoe DJ, Wolfe MS. Transition-state analogue inhibitors of gamma–secretase bind directly to presenilin-1. Nat Cell Biol Jul. 2000;2(7):428–434.

Esler WP, Kimberly WT, Ostaszewski BL, Diehl TS, Moore CL, Tsai JY, Rahmati T, Xia W, Selkoe DJ, Wolfe MS. Transition-state analogue inhibitors of gamma–secretase bind directly to presenilin-1. Nat Cell Biol Jul. 2000;2(7):428–434.

Ran Q, Pereira–Smith OM. Identification of an alternatively spliced form of the Tat interactive protein (Tip60), Tip60(beta). Gene Nov. 27, 2000;258(1–2):141–146.

Struhl G, Adachi A. Requirements for presenilin–dependent cleavage of notch and other transmembrane proteins. Mol Cell Sep. 2000;6(3):625–636.

Yan Y, Barlev NA, Haley RH, Berger SL, Marmorstein R. Crystal structure of yeast Esa1 suggests a unified mechanism for catalysis and substrate binding by histone acetyltransferases. Mol Cell Nov. 2000;6(5):1195–1205.

Zwahlen C, Li SC, Kay LE, Pawson T, Forman–Kay JD. Multiple modes of peptide recognition by the PTB domain of the cell fate determinant Numb. EMBO J Apr. 3, 2000;19(7):1505–1515.

Bayer TA, Cappai R, Masters CL, Beyreuther K, Multhaup G. It all sticks together—the APP–related family of proteins and Alzheimer's disease. Mol Psychiatry Nov. 1999;4(6):524–528.

Bing Z, Reddy SA, Ren Y, Qin J, Liao WS. Purification and characterization of the serum amyloid A3 enhancer factor. J Biol Chem Aug. 27, 1999;274(35):24649–24656.

De Strooper B, Annaert W, Cupers P, Saftig P, Craessaerts K, Mumm JS, Schroeter EH, Schrijvers V, Wolfe MS, Ray WJ, Goate A, Kopan R. A presenilin-1-dependent gamma–secretase–like protease mediates release of Notch intracellular domain. Nature Apr. 8, 1999;398(6727):518–522.

Haass C, De Strooper B. The presenilins in Alzheimer's disease—proteolysis holds the key. Science Oct. 29, 1999;286(5441):916–919.

Struhl G, Greenwald I. Presenilin is required for activity and nuclear access of Notch in Drosophila. Nature Apr. 8, 1999;398(6727):522–525.

Ye Y, Lukinova N, Fortini ME.Neurogenic phenotypes and altered Notch processing in Drosophila Presenilin mutants. Nature Apr. 8, 1999;398(6727):525–529.

Ermekova KS, Chang A, Zambrano N, de Candia P, Russo T, Sudol M. Proteins implicated in Alzheimer disease. The role of FE65, a new adapter which binds to beta–amyloid precursor protein. Adv Exp Med Biol 1998;446:161–80.

McLoughlin DM, Irving NG, Miller CC. The Fe65 and X11 families of proteins: proteins that interact with the Alzheimer's disease amyloid precursor protein. Biochem Soc Trans Aug. 1998;26(3):497–500.

Price DL, Tanzi RE, Borchelt DR, Sisodia SS. Alzheimer's disease: genetic studies and transgenic models. Annu Rev Genet 1998;32:461–493.

Selkoe DJ. The cell biology of beta–amyloid precursor protein and presenilin in Alzheimer's disease. Trends Cell Biol Nov. 1998;8(11):447–453.

Zambrano N, Minopoli G, de Candia P, Russo T. The Fe65 adapter protein interacts through its PID1 domain with the transcription factor CP2/LSF/LBP1. J Biol Chem Aug. 7, 1998;273(32):20128–20133.

Ermekova KS, Zambrano N, Linn H, Minopoli G, Gertler F, Russo T, Sudol M. The WW domain of neural protein FE65 interacts with proline–rich motifs in Mena, the mammalian homolog of Drosophila enabled. J Biol Chem Dec. 26, 1997;272(52):32869–32877.

Okamoto M, Sudhof TC. Mints, Munc18–interacting proteins in synaptic vesicle exocytosis. J Biol Chem Dec. 12, 1997;272(50):31459–64.

Peraus GC, Masters CL, Beyreuther K. Late compartments of amyloid precursor protein transport in SY5Y cells are involved in beta–amyloid secretion. J Neurosci Oct. 15, 1997;17(20):7714–7724.

Zambrano N, Buxbaum JD, Minopoli G, Fiore F, De Candia P, De Renzis S, Faraonio R, Sabo S, Cheetham J, Sudol M, Russo T. Interaction of the phosphotyrosine interaction/phosphotyrosine binding–related domains of Fe65 with wild–type and mutant Alzheimer's beta–amyloid precursor proteins. J Biol Chem Mar. 7, 1997;272(10):6399–6405.

Borg JP, Ooi J, Levy E, Margolis B. The phosphotyrosine interaction domains of X11 and Fe65 bind to distinct sites on the YENPTY motif of amyloid precursor protein. Mol Cell Biol Nov. 1996;16(11):6229–6241.

Guenette SY, Chen J, Jondro PD, Tanzi RE. Association of a novel human FE65–like protein with the cytoplasmic domain of the beta–amyloid precursor protein. Proc Natl Acad Sci USA Oct. 1, 1996;93(20):10832–10837.

Kamine J, Elangovan B, Subramanian T, Coleman D, Chinnadurai G. Identification of a cellular protein that specifically interacts the essential cysteine region of the HIV–1 Tat transactivator. Virology Feb. 15, 1996;216(2):357–366.

McLoughlin DM, Miller CC. The intracellular cytoplasmic domain of the Alzheimer's disease amyloid precursor protein interacts with phosphotyrosine–binding domain proteins in the yeast two–hybrid system. FEBS Lett Nov. 18, 1996;397(2–3):197–200.

Fiore F, Zambrano N, Minopoli G, Donini V, Duilio A, Russo T. The regions of the Fe65 protein homologous to the phosphotyrosine interaction/phosphotyrosine binding domain of Shc bind the intracellular domain of the Alzheimer's amyloid precursor protein. J Biol Chem Dec. 29, 1995;270(52):30853–30856.

Hollenberg SM, Sternglanz R, Cheng PF, Weintraub H. Identification of a new family of tissue–specific basic Helix–Loop–Helix proteins with a two–hybrid system. Mol. Cell. Biol. 1995;15:3813–3822.

Hata Y, Slaughter CA, Sudhof TC. Synaptic vesicle fusion complex contains unc–18 homologue bound to syntaxin. Nature Nov. 25, 1993;366(6453):347–351.

Ushkaryov YA, Petrenko AG, Geppert M, Sudhof TC. Neurexins: synaptic cell surface proteins related to the alpha–latrotoxin receptor and laminin. Science Jul. 3, 1992;257(5066):50–56.

Stringer KF, Ingles CJ, Greenblatt J. Direct and selective binding of an acidic transcriptional activation domain to the TATA–box factor TFIID. Nature Jun. 28, 1990;345(6278): 783–786.

Fields S, Song O. A novel genetic system to detect protein–protein interactions. Nature Jul. 20,1989;340(6230):245–246.

Lillie JW, Green MR. Transcription activation by the adenovirus E1a protein. Nature (London) 1989;338:39–44.

Sadowski I, Ma J, Triezenberg S, Ptashne M. GAL4–VP16 is an unusually potent transcriptional activator. Nature Oct. 6, 1988;335(6190):563–564.

Smith GM, Mileham KA, Cooke SE, Woolston SJ, George HK, Charles AD, Brammar WJ. The *Escherichia coli* LexA repressor–operator system works in mammalian cells. EMBO J Dec. 1, 1988;7(12):3975–3982.

Kang J, Lemaire HG, Unterbeck A, Salbaum JM, Masters CL, Grzeschik KH, Multhaup G, Beyreuther K, Muller–Hill B. The precursor of Alzheimer's disease amyloid A4 protein resembles a cell–surface receptor. Nature Feb. 19–25, 1987;325(6106):733–736.

Hurstel S, Granger–Schnarr M, Daune M, Schnarr M. In vitro binding of LexA repressor to DNA: evidence for the involvement of the amino–terminal domain. EMBO J Apr. 1986;5(4):793–798.

Giniger E, Varnum SM, Ptashne M. Specific DNA binding of GAL4, a positive regulatory protein of yeast. Cell Apr. 1985;40(4):767–774.

Silver PA, Keegan LP, Ptashine M. Amino terminus of the yeast GAL4 gene product is sufficient for nuclear localization. Proc Natl Acad Sci USA Oct. 1984;81(19):5951–5955.

Vojtek AB, Hollenberg SM, Cooper JA. Mammalian Ras interacts directly with the serine/threonine kinase Raf. Cell Jul. 16, 1993;74(1):205–214.

* cited by examiner

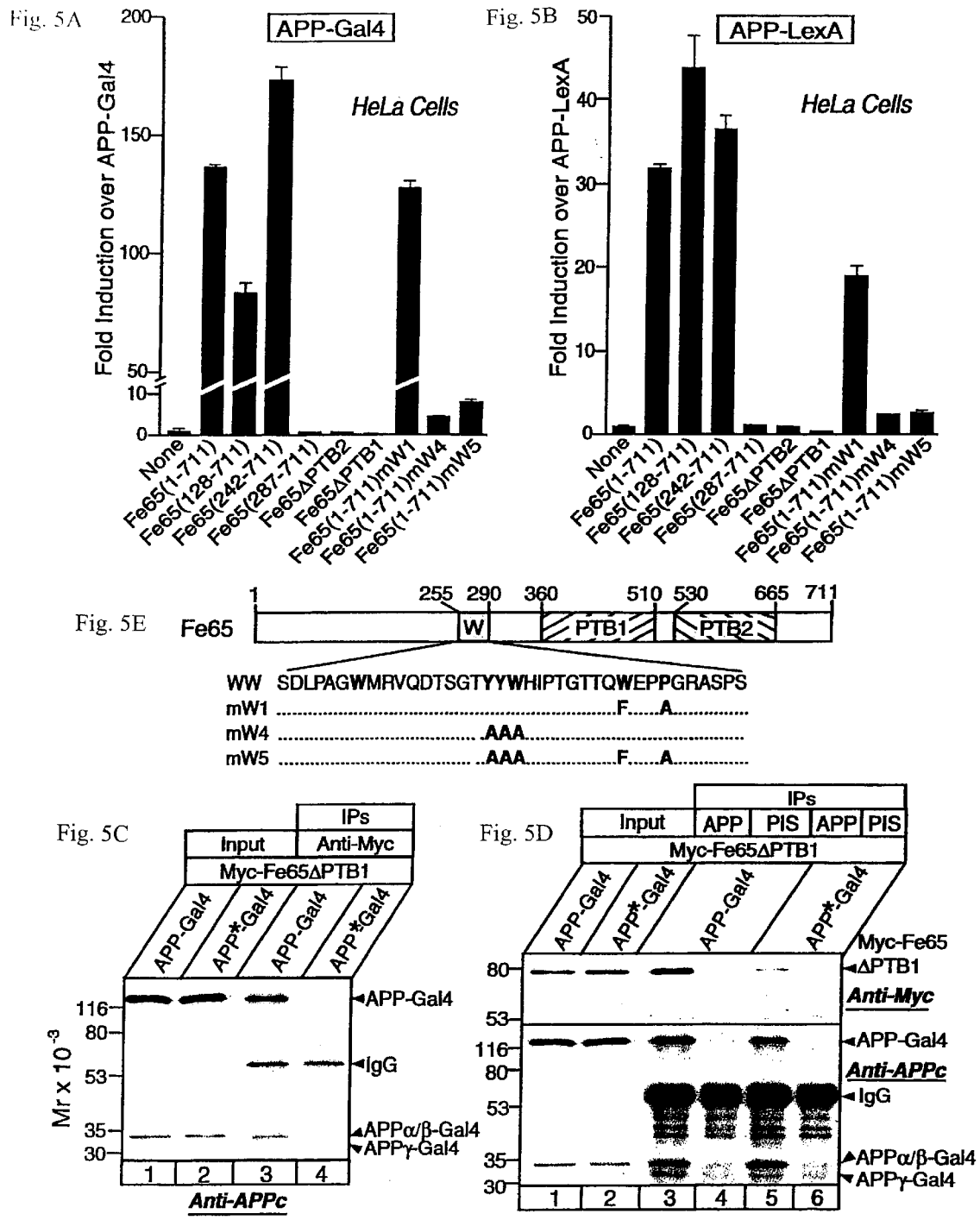

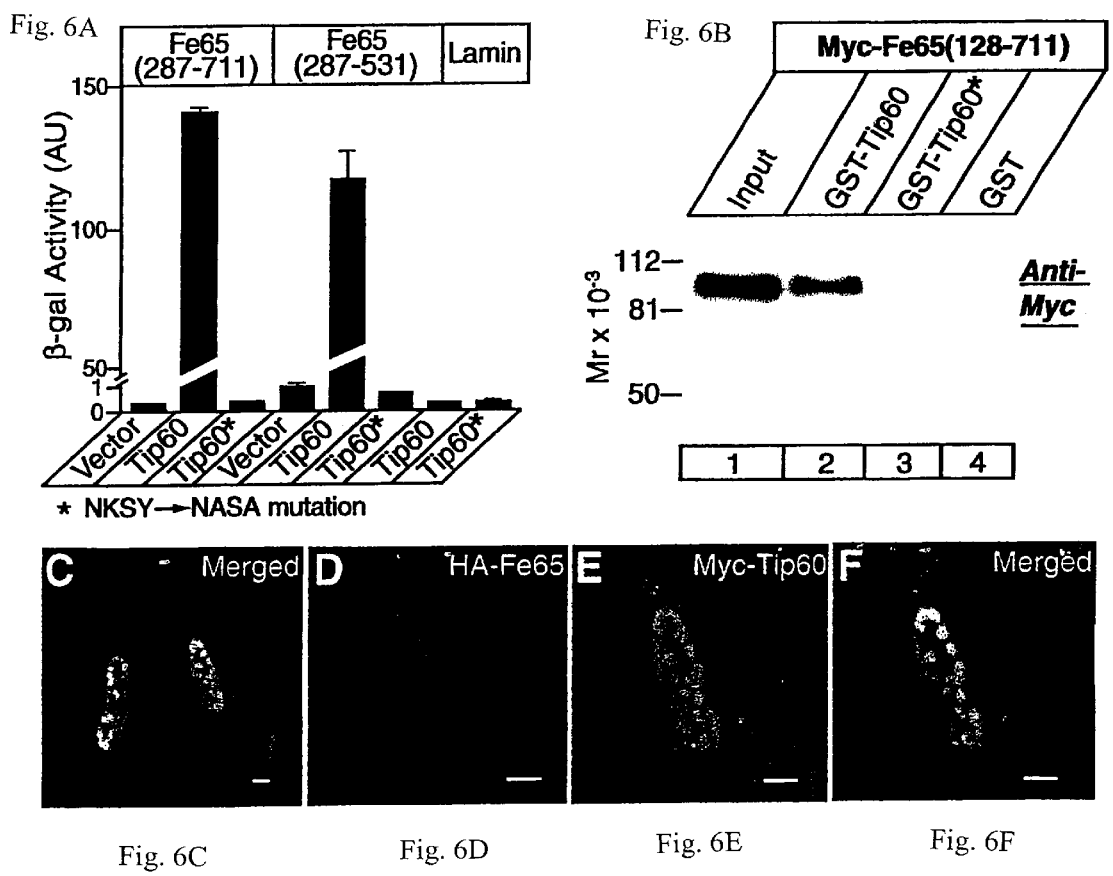

SEQUENCE LISTING

<160> NUMBER OF SEQ ID NOS: 16

<210> SEQ ID NO 1
<211> LENGTH: 13
<212> TYPE: PRT
<213> ORGANISM: artificial sequence
<220> FEATURE:
<223> OTHER INFORMATION: synthetic peptide

<400> SEQUENCE: 1

```
    Gln Leu Thr Val Ser Pro Glu Phe Ala Pro Pro Thr Asp
    1               5                  10
```

<210> SEQ ID NO 2
<211> LENGTH: 15
<212> TYPE: PRT
<213> ORGANISM: artificial sequence
<220> FEATURE:
<223> OTHER INFORMATION: synthetic peptide

<400> SEQUENCE: 2

```
Asp Glu Tyr Gly Gly Gly Ile Pro Pro Gly Gln Tyr Thr Ser Ile
1               5                   10                  15
```

<210> SEQ ID NO 3
<211> LENGTH: 16
<212> TYPE: PRT
<213> ORGANISM: artificial sequence
<220> FEATURE:
<223> OTHER INFORMATION: synthetic peptide

<400> SEQUENCE: 3

```
Met Leu Lys Lys Lys Pro Leu Ala Ser Ser Arg Met Lys Leu Leu Ser
1               5                   10                  15
```

<210> SEQ ID NO 4
<211> LENGTH: 19
<212> TYPE: PRT
<213> ORGANISM: artificial sequence
<220> FEATURE:
<223> OTHER INFORMATION: synthetic peptide

```
<400> SEQUENCE: 4

Gln Leu Thr Val Ser Pro Glu Phe Pro Gly Ile Pro Pro Gly Gln Tyr
 1               5                  10                  15

Thr Ser Ile

<210> SEQ ID NO 5
<211> LENGTH: 16
<212> TYPE: PRT
<213> ORGANISM: artificial sequence
<220> FEATURE:
<223> OTHER INFORMATION: synthetic peptide

<400> SEQUENCE: 5

Met Tyr Lys Tyr Arg Thr Leu Ala Ser Ser Arg Met Lys Leu Leu Ser
 1               5                  10                  15

<210> SEQ ID NO 6
<211> LENGTH: 15
<212> TYPE: PRT
<213> ORGANISM: artificial sequence
<220> FEATURE:
<223> OTHER INFORMATION: synthetic peptide

<400> SEQUENCE: 6

Asp Glu Tyr Gly Gly Gly Ile Pro Pro Gly Tyr Lys Tyr Arg Asn
 1               5                  10                  15

<210> SEQ ID NO 7
<211> LENGTH: 19
<212> TYPE: PRT
<213> ORGANISM: artificial sequence
<220> FEATURE:
<223> OTHER INFORMATION: synthetic peptide

<400> SEQUENCE: 7

Gln Leu Thr Val Ser Pro Glu Phe Pro Gly Ile Pro Pro Gly Tyr Lys
 1               5                  10                  15

Tyr Arg Asn

<210> SEQ ID NO 8
<211> LENGTH: 12
<212> TYPE: PRT
<213> ORGANISM: artificial sequence
<220> FEATURE:
<223> OTHER INFORMATION: synthetic peptide

<400> SEQUENCE: 8

Glu Gly Ser Tyr His Ile Asp Asp Ala Ala Val Thr
 1               5                  10

<210> SEQ ID NO 9
<211> LENGTH: 11
<212> TYPE: PRT
<213> ORGANISM: artificial sequence
<220> FEATURE:
<223> OTHER INFORMATION: synthetic peptide

<400> SEQUENCE: 9

Glu Gln Met Gln Asn Ile Asp Glu Ser Arg Asn
 1               5                  10

<210> SEQ ID NO 10
<211> LENGTH: 18
<212> TYPE: PRT
```

```
<213> ORGANISM: artificial sequence
<220> FEATURE:
<223> OTHER INFORMATION: synthetic peptide

<400> SEQUENCE: 10

Asn Gly Asp Trp Leu Glu Phe Pro Gly Ile Pro Pro Gly Gln Tyr Thr
 1               5                  10                  15
Ser Ile

<210> SEQ ID NO 11
<211> LENGTH: 14
<212> TYPE: PRT
<213> ORGANISM: artificial sequence
<220> FEATURE:
<223> OTHER INFORMATION: synthetic peptide

<400> SEQUENCE: 11

Met Leu Lys Lys Lys Pro Leu Ala Lys Met Lys Ala Leu Thr
 1               5                  10

<210> SEQ ID NO 12
<211> LENGTH: 4
<212> TYPE: PRT
<213> ORGANISM: artificial sequence
<220> FEATURE:
<223> OTHER INFORMATION: synthetic peptide

<400> SEQUENCE: 12

Asn Lys Ser Tyr
 1

<210> SEQ ID NO 13
<211> LENGTH: 4
<212> TYPE: PRT
<213> ORGANISM: artificial sequence
<220> FEATURE:
<223> OTHER INFORMATION: synthetic peptide

<400> SEQUENCE: 13

Asn Ala Thr Ala
 1

<210> SEQ ID NO 14
<211> LENGTH: 4
<212> TYPE: PRT
<213> ORGANISM: artificial sequence
<220> FEATURE:
<223> OTHER INFORMATION: synthetic peptide

<400> SEQUENCE: 14

Asn Ala Ser Ala
 1

<210> SEQ ID NO 15
<211> LENGTH: 4
<212> TYPE: PRT
<213> ORGANISM: artificial sequence
<220> FEATURE:
<223> OTHER INFORMATION: synthetic peptide

<400> SEQUENCE: 15

Asn Lys Ser Tyr
 1

<210> SEQ ID NO 16
<211> LENGTH: 37
```

-continued

```
<212> TYPE: PRT
<213> ORGANISM: artificial sequence
<220> FEATURE:
<223> OTHER INFORMATION: synthetic peptide

<400> SEQUENCE: 16

Ser Asp Leu Pro Ala Gly Trp Met Arg Val Gln Asp Thr Ser Gly Thr
1               5                   10                  15

Tyr Tyr Trp His Ile Pro Thr Gly Thr Thr Gln Trp Glu Pro Pro Gly
            20                  25                  30

Arg Ala Ser Pro Ser
            35
```

METHODS OF IDENTIFYING AGENTS THAT AFFECT CLEAVAGE OF AMYLOID-β PRECURSOR PROTEIN

BACKGROUND OF THE INVENTION

Alzheimer's disease is a degenerative brain disorder that is characterized clinically by progressive loss of memory and cognitive impairment. Pathologically, the disease is characterized by lesions comprising neurofibrillary tangles, cerebrovascular amyloid deposits, and neuritic plaques. The cerebrovascular amyloid deposits and neuritic plaques contain amyloid-β peptide. The aggregation of amyloid-β peptide is instrumental in the pathogenesis of Alzheimer's disease.

Amyloid-β peptide is derived from amyloid-β precursor protein (APP). APP is a cell-surface protein with a large N-terminal extracellular sequence, a single transmembrane region (TMR) and a short C-terminal cytoplasmic tail. APP is processed by proteolysis in all cells. Initially, α- and β-secretases cleave APP at defined extracellular sequences just outside of the TMR to release a large N-terminal extracellular fragment. Thereafter, γ-secretase cuts APP in the middle of the TMR to generate small extracellular peptides and a C-terminal fragment comprising half of the TMR and the full cytoplasmic tail. See, e.g., Selkoe (1998) Trends Cell Biol. 8, 447–453; Bayer et al. (1999) Mol. Psychiatry 4, 524; Haass et al. (1999) Science 286, 916–919; Price et al. (1998) Ann. Rev. Gevet 32, 461–493.

Cleavage of APP by β- and γ-secretase produces the amyloid-β peptides (AP40 and AP42) implicated in the pathogeneses of Alzheimer's disease. Various methods for the diagnosis and monitoring of the disease involve assessing the cleavage of APP and detection of amyloid-β peptide. However, these methods suffer from various disadvantages including the insolubility of amyloid-β peptide, cross-reactivity of antibodies against the peptide with the precursor APP, and different levels of protease activity in different body fluids.

The γ-cleavage of APP is mediated by presenilins, intrinsic membrane proteins that may correspond to γ-secretase and that are mutated in some cases of familial Alzheimer's disease. See, e.g., Esler et al. (2000) Nat. Cel. Biol. 2, 428–434. Also, γ-cleavage occurs in APP-homologs that are not implicated in Alzheimer's disease. For example, Notch proteins are membrane proteins that are also cleaved in the middle of the TMR in a presenilin-dependent reaction. See, e.g. Ye et al. (1999) Nature 398, 525–529; De Strooper et al. (1999) Nature 398, 518–522; Struhl et al. (1999) Nature 398, 522–525. Notch proteins are cell-surface proteins involved in intercellular signaling in which presenilin-dependent cleavage liberates a cytoplasmic fragment that functions in nuclear transcription. Struhl et al. (2000) Mol. Cell 6, 625–636. Sterol regulatory element binding proteins (SREPPs) are also cleaved in the TMRs to generate nuclear transcription factors. Brown et al. (2000) Cell 100, 391–398. In contrast, the physiological significance of γ-cleavage of APP, and in particular the biological role of the cytoplasmic tail fragment, has heretofore been unclear. In accordance with the present invention it has been discovered that the cytoplasmic tail forms a functional complex with nuclear proteins, and that the complex is a potent stimulator of transcription. The present invention thus provides new methods for identifying agents that affect the cleavage of APP.

SUMMARY OF THE INVENTION

The present invention provides a method of identifying an agent that affects the cleavage of APP comprising contacting a cell containing APP modified in the C-terminal cytoplasmic tail to allow detection of nuclear localization with a candidate agent and measuring nuclear localization of a C-terminal cytoplasmic cleavage product of APP in the presence and absence of the agent.

In another embodiment, the present invention provides a method of identifying an agent that affects the cleavage of APP comprising providing a cell containing APP and a protein that interacts with the C-terminal cytoplasmic cleavage product of APP to regulate transcription, wherein the protein is modified to allow detection of nuclear localization of the C-terminal cytoplasmic cleavage product of APP; contacting the cell with a candidate agent; and measuring nuclear localization of the C-terminal cytoplasmic cleavage product of APP in the presence and absence of the agent.

The invention further provides agents identified by the foregoing method, and compositions comprising the agents.

In another embodiment, the invention is directed to vectors, transfected cells and kits useful for identifying an agent that affects the cleavage of APP.

BRIEF DESCRIPTION OF THE DRAWINGS

FIGS. 1A–C show results of Gal4-transactivation assays in PC12 cells (FIG. 1A) and HEK293 cells (FIG. 1B) and the domain structures of proteins encoded by the test plasmids (FIG. 1C). Test plasmids are identified by numbers below the bars in FIGS. 1A and 1B. Luciferase activity was normalized for β-galactosidase activity to control for translation efficiency. In FIG. 1A, luciferase activity was additionally normalized for the activity of cells co-transfected with Gal4 alone. FIGS. 1A and 1B show results from representative experiments.

FIGS. 5A–E show transactivation using full length APP-Gal4 (FIG. 5A) and APP-LexA (FIG. 5B) fusion proteins co-transfected with corresponding reporter plasmids and a β-galactosidase control plasmids. Various Fe65 proteins described below the bar diagrams were co-transfected with the test and control plasmids. Transactivation is expressed as fold induction over transfection with Gal4-APP or LexA-APP alone. The domain structure of Fe65 and deletion mutants of Fe65 are shown in FIG. 5E. WW=SEQ ID NO:16. FIGS. 5C and D show results of immunoprecipitations carried out with antibodies to the myc-epitope (FIG. 5C) or to APP (FIG. 5D; PIS=preimmune serum) and analyzed by immunoblotting with antibodies to APP (FIG. 5C and lower part of FIG. 5D) or to myc (upper part of FIG. 5D). The positions of the various proteins are indicated on the right of the immunoblots, and the locations of molecular weight standards are shown on the left.

FIGS. 6A–F demonstrate the interaction of Fe65 with Tip60. FIG. 6A shows results of a quantitative yeast two-hybrid assay. FIG. 6B shows GST-pulldowns of myc-tagged Fe65 expressed in COS cells with wild-type and mutant GST-Tip60 proteins. FIGS. 6C–F show immunofluorescence localization of tagged HA-Fe65 and myc-tagged Tip60 co-transfected into HeLa cells. FIG. 6C shows an overview of two adjacent cells; FIGS. 6D–F display individual and merged labeling patterns. Calibration bars=10 µM.

DETAILED DESCRIPTION OF THE INVENTION

Figure 1C:
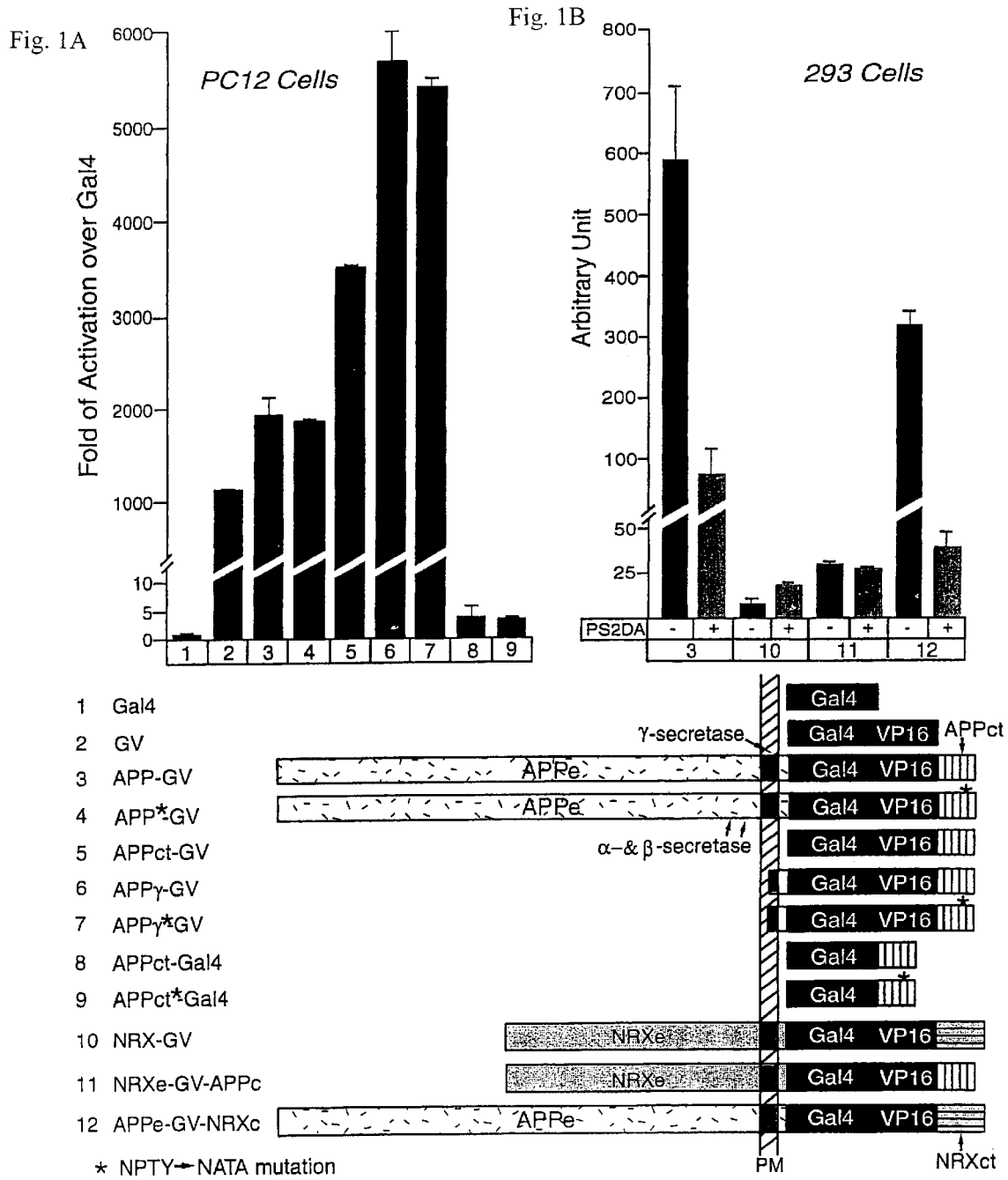

Proteolytic processing of APP produces, inter alia, amyloid-β peptide that contributes to the pathogenesis of Alzheimer's disease, and a C-terminal cytoplasmic tail of APP of unknown function until the present invention. In accordance with the present invention, it has been discovered that the C-terminal cytoplasmic tail of APP engages in nuclear signaling. In particular, it has been discovered that the released cytoplasmic tail of APP forms a functional complex with the nuclear protein Fe65 and the histone acetyl-transferase Tip 60, and that the complex is a potent stimulator of transcription by heterologous DNA-binding domains. This understanding of the role of the cytoplasmic tail of APP in nuclear signaling has led to the development of an assay to identify agents that affect the cleavage of APP. Such agents are useful as candidate therapeutics for the treatment of Alzheimer's disease, and as models for rational drug design.

In one embodiment, the present invention provides a method of identifying an agent that affects the cleavage of APP comprising contacting a cell, wherein the cell contains APP modified in the C-terminal cytoplasmic tail to allow detection of nuclear localization, with a candidate agent and measuring nuclear localization of the C-terminal cytoplasmic cleavage product of APP in the presence and absence of a candidate agent. An agent that increases or decreases the nuclear localization of the cleavage product relative to nuclear localization in the absence of the agent is defined as an agent that affects cleavage of APP.

The term APP as used herein includes naturally occurring mammalian APP and also APP that has been modified, for example in a way to facilitate measurement of nuclear localization of a cleavage product. Naturally occurring human APP is a 695 amino acid protein, in which the C-terminal 47 residues are designated the cytoplasmic tail. The gene encoding APP, its splice variants, and resulting nucleotide and amino acid sequences are known in the art and disclosed for example by Kang et al. (1987) Nature 325, 733–736, Selkoe, supra; Bayer et al., supra; Haass et al., supra; and Price et al., supra the disclosures of which are incorporated herein by reference.

Further, APP as defined herein may include other modifications such as insertions, deletions and substitutions provided that the functions of ability of the cytoplasmic tail or part thereof to be cleaved from the remainder of APP and translocated to the nucleus are retained.

The C-terminal cytoplasmic tail of APP is modified to allow detection of nuclear localization. The modification may be in any region of the cytoplasmic tail. The modification may be at the C-terminal or N-terminal end of the tail, for example at the junction of the transmembrane and cytoplasmic domains. In one embodiment, the cytoplasmic tail of APP is modified to include the DNA binding domain and the activation domain of the same or different heterologous transcription factors. Heterologous as used herein means not derived from a gene encoding APP. In this embodiment, nuclear localization is measured by determining activation of transcription of an indicator gene that is under the transcriptional control of a binding site for the DNA binding domain. Transcription factors and their component DNA-binding and activation domains are well-known in the art.

In a preferred embodiment, the cytoplasmic tail is modified to include a heterologous DNA-binding domain such as the DNA-binding domain of the yeast transcription factor Gal4, or the bacterial LexA DNA binding domain. The Gal4 and LexA DNA binding domains are known in the art and disclosed for example by Giniger et al. (1985) Cell 40, 767–774 and Hurstel et al. (1986) EMBO J. 5, 793–798. The modification may further contain the transcriptional activation domain of Gal4, or another activator such as the viral VP16 activator, which is disclosed for example by Stringer et al. (1990) Nature 345, 783–786. In a preferred embodiment, the cytoplasmic tail of APP is modified to include Gal4 and VP16. A transcription factor module of Gal4-VP16 is described by Sadowski et al. (1988) Nature 335, 563–564. In an alternative embodiment, a DNA-binding domain but not an activation domain is included with the cytoplasmic tail and the mammalian nuclear multidomain protein, Fe65, is added as a co-factor to facilitate transcriptional activation. Fe65 is known in the art and disclosed for example by Duilio et el. (1991) Nucleic Acids Res. 19, 5269–5274. The term Fe65 as used herein includes modifications such as insertions, deletions and substitutions provided that the function of the ability of Fe65 to facilitate transcriptional activation is maintained. For example, it has been demonstrated herein that the N-terminal third of Fe65 may be deleted without loss of this function.

Accordingly, the modification of the cytoplasmic tail may consist of a heterologous DNA-binding domain, or a module consisting of a DNA-binding domain and a transcriptional activation domain, which may be from the same or different sources.

The indicator gene is operably linked to a binding site for the DNA-binding protein. For example, the indicator gene may be provided in the form of a Gal4 or LexA dependent reporter plasmid containing an indicator gene such as luciferase or chloramphenicol acetyl transferase under the control of a Gal4 or LexA regulatory element, respectively, such as an upstream activating sequence. Translocation of the cytoplasmic tail of APP to the nucleus results in translocation of the transcription factor as well, resulting in activation of transcription of the marker gene. Accordingly, detection of the marker gene product provides an assay for nuclear localization of the cytoplasmic tail of APP, and hence measures cleavage of APP. Transcriptional activation assays are described by Fields et al. (1989) Nature 340, 245–246, the disclosure of which is incorporated herein by reference. Gal4 and LexA reporter plasmids are described by Lillie et al. (1989) Nature (London) 338, 38–44 and Hollenberg et al. (1995) Mol. Cell. Biol. 15:3813–3822.

Candidate agents that may be tested by the assays of the present invention include proteins, peptides, non-peptide small molecules, and any other source of therapeutic candidate agents. The agents may be naturally occurring or synthetic, and may be a single substance or a mixture. Screening may be performed in high throughput format using combinatorial libraries, expression libraries and the like. Agents identified as affecting APP cleavage may be subsequently tested for biological activity and used as therapeutics or as models for rational drug design.

Cells useful for the assays of the present invention include eukaryotic cells in which the cytoplasmic tail cleavage product of APP can be translocated to the nucleus. Suitable cells include, for example, insect and mammalian cells. Preferred cells include Schneider, PC12, COS, HeLa and HEK293 cells.

Cells containing APP may be cells stably or transiently transfected with a construct encoding APP as described above using methods known to those of ordinary skill in the art. Constructs containing chimeric genes comprising a promoter operably linked to nucleic acid encoding APP and modified to include the DNA-binding domain of a transcriptional activator, or a module comprising the DNA-binding domains and transcriptional activation domain of the same or different transcription factor, are constructed using well-known recombinant DNA methods. These constructs are co-transfected into cells with the corresponding reporter constructs described above. For cases in which the construct does not contain a transcriptional activation domain, cells are also co-transfected with vector comprising a nucleic acid encoding Fe65 operably linked to a promoter. The promoter may be constitutive or inducible.

The transfected cells are contacted with an agent to be tested for its ability to affect APP cleavage. A detectable increase or decrease in nuclear localization of the C-terminal cytoplasmic tail, as measured by a change in transcriptional activation of the indicator gene, is indicative of an agent that affects cleavage of APP. The cells may be contacted with the candidate agent before expression of modified APP is induced from an inducible promoter.

In a particularly preferred embodiment of the present invention human APP is modified to include Gal4-VP16 within the cytoplasmic tail. In particular, Gal4-VP16 is inserted between residues 651 and 652 of APP. The modified APP is generated by means of a mammalian expression plasmid containing a chimeric gene encoding residues 1–651 of APP, Gal4, VP16, and residues 652–695 of APP (i.e. the cytoplasmic tail, APP ct) under the control of a promoter. The plasmid may further comprise regulatory sequences, linkers, and other elements to facilitate cloning, replication, transfection and expression. A cell comprising the modified APP is provided by transfecting a cell, preferably a mammalian cell, and most preferably a human cell, with the expression plasmid. The cell is cotransfected with a Gal4 reporter plasmid in which luciferase mRNA is driven by multiple copies of the Gal4 upstream activating sequence (UAS). When the modified APP is cleaved by γ-secretase, the cleavage product containing Gal4-VP16 enters the nucleus and transactivates transcription from the Gal4 reporter plasmid. Expression of luciferase is measured by standard assays, for example by measuring luciferase activity using a commercially available kit. Luciferase expression is a measure of transactivation, which is in turn a measure of APP cleavage.

The transfected cells are contacted with a candidate agent, and luciferase expression is measured in the presence and absence of the agent. An agent that increases or decreases luciferase expression is an agent that affects APP cleavage.

In another embodiment, the present invention provides a method of identifying an agent that affects the cleavage of APP comprising providing a cell, wherein the cell contains APP and a protein that interacts with the C-terminal cleavage product of APP in the nucleus to activate transcription, and wherein the protein is modified to allow detection of nuclear translocation of the C-terminal cytoplasmic cleavage product; contacting the cell with a candidate agent; and measuring nuclear localization of the C-terminal cytoplasmic cleavage product in the presence and absence of the agent. An agent that increases or decreases nuclear localization of the C-terminal cleavage product relative to nuclear localization in the absence of the cleavage product is defined as an agent that affects cleavage of APP.

In accordance with the present invention, it has been discovered that the C-terminal cytoplasmic cleavage product of APP may interact with one or more other proteins to activate transcription. Accordingly, cleavage of APP can be detected by modifying a protein that interacts, directly or indirectly, with the cleavage product. Direct interaction refers to proteins that form a complex with the cleavage product. Indirect action includes proteins that interact with other proteins that are targets of the cleavage product, and thereby includes, for example, proteins that interact with Fe65 and/or Tip60 in the regulation of transcription. A preferred protein is the histone acetyl-transferase Tip60. In a preferred embodiment of this method, a protein that interacts with the C-terminal cleavage product of APP to activate transcription, for example Tip60 is modified to allow detection of nuclear localization, for example by fusion with the DNA binding domain of a transcriptional activator such as Gal4 or LexA. Nuclear localization is measured by determining activation of transcription of an indicator gene that is under the transcriptional control of a binding site for the DNA binding domain, as described hereinabove.

The nucleotide and amino acid sequences of Tip60 are known in the art and disclosed for example by Kamine et al. (1996) Virology 216, 357–366 and Ran et al. (2000) Gene 258, 141–146. The term Tip60 as used herein includes modifications such as insertions, deletions and substitutions provided that the ability of Tip60 to interact with the C-terminal cytoplasmic cleavage product of APP is maintained.

In a preferred embodiment of this method, the cells contain APP, Fe65 and Tip60 modified to contain the DNA binding domain of a transcriptional activator, preferably Gal4. Such cells may be obtained by co-transfection with plasmids containing nucleic acids encoding APP, Fe65, and modified Tip60. Plasmids may further comprise regulatory sequences, linkers and other elements to facilitate cloning, replication, transfection and expression. Cells are eukaryotic, including for example insect and mammalian, and preferably human. Cells are also co-transfected with the appropriate reporter plasmid as described above. Expression of the reporter gene is a measure of transactivation, which is in turn a measure of nuclear localization of the C-terminal cytoplasmic cleavage product of APP, and thus APP cleavage. Reporter gene expression is measured as described hereinabove.

In another embodiment the present invention provides vectors that contain nucleic acids encoding the modified APP. In a preferred embodiment, the vector comprises a nucleic acid encoding APP operably linked to a promoter wherein a nucleic acid module encoding a heterologous DNA binding domain of a transcription factor and a transcriptional activator of the same or a different transcription factor is contained within the portion of the nucleic acid that encodes the C-terminal cytoplasmic tail of APP. A module "within" the tail includes embodiments in which the module is at the 5'-end or 3'-end of the region encoding the cytoplasmic tail. In a preferred embodiment the module is Gal4-VP16. The vectors may further comprise regulatory sequences, linkers, and other elements to facilitate cloning, replication, transfection and expression.

The present invention further provides vectors that comprise a nucleic acid encoding APP operably linked to a promoter wherein a nucleic acid encoding a heterologous DNA binding domain of a transcription factor is contained with the portion of the nucleic acid that encodes the C-terminal cytoplasmic tail of APP. The DNA binding domain may be at the 5'-end or 3'-end of the region encoding the cytoplasmic tail. In a preferred embodiment the DNA binding domain is Gal4. The vectors may further comprise regulatory sequences, linkers, and other elements to facilitate cloning, replication, transfection and expression.

The present invention further provides vectors that comprise a nucleic acid encoding Tip60 and the DNA binding domain of a transcription factor wherein the nucleic acid is operably linked to a promoter. In a preferred embodiment the DNA binding domain is Gal4. The vectors may further comprise regulatory sequences, linkers, and other elements to facilitate cloning, replication, transfection and expression.

The present invention further provides cells containing the foregoing vectors. The cells are eukaryotic, preferably mammalian, and most preferably human. Cells containing the vectors of the invention may be obtained by methods known in the art, and may be transiently or stably transfected. The cells may also further contain a corresponding reporter plasmid as described hereinabove.

In another embodiment, the present invention provides agents that affect cleavage of APP identified by the method of the present invention. Compositions comprising the agents are also provided. The compositions may comprise carriers and/or diluents such as solvents, dispersion media, antibacterial and antifungal agents, microcapsules, liposomes, cationic lipid carriers, isotonic and absorption delaying agents and the like, as well as supplementary active ingredients.

The present invention further provides kits useful for identifying an agent that affects cleavage of APP. The kits comprise a first compartment containing cells comprising a vector that encodes a modified APP of the invention. The cells may further contain a reporter plasmid. The kits may further comprise a second compartment containing a means for measuring expression of an indicator gene contained in the reporter plasmid.

In another embodiment, the kits comprise a first compartment containing a vector that encodes a modified APP of the invention. The kits may further comprise a second compartment containing a reporter plasmid, and may further comprise a third compartment containing cells suitable for transfection by the vector of the first compartment.

In a further embodiment, the kits comprise a first compartment containing a vector comprising a nucleic acid encoding APP operably linked to a promoter, a second compartment containing a vector comprising a nucleic acid encoding Fe65 operably linked to a promoter, and a third compartment containing a nucleic acid encoding a fusion protein comprising Tip60 and the DNA binding domain of a transcriptional activator, preferably Gal4.

The following nonlimiting examples serve to further illustrate the present invention.

EXAMPLE I

Materials and Methods

The following materials and methods were used in subsequent examples.
1. Transactivation Assays
1.1 General Design PC12, COS, HeLa, and HEK293 cells were co-transfected at 50–80% confluency in 6-well plates using Fugene6 (Roche, Indianapolis, Ind.), and 3–4 plasmids (0.1–1.0 µg DNA/well depending on cell types; see plasmid list below for description of all constructs). All transfections included a. Gal4 (pG5E1B-luc) or LexA (pL8G5-luc) reporter plasmids; b. constitutively expressed β-galactosidase expression plasmid (pCMV-LacZ) to control for transfection efficiency; and c. the Gal4- or LexA-fusion protein vectors. Cells were harvested 48 hr post-transfection in 0.2 ml/well reporter lysis buffer (Promega, Madison, Wis.), and their luciferase and β-galactosidase activities were determined with the Promega luciferase assay kit and the standard O-nitrophenyl-D-galacto-pyranoside method, respectively. The luciferase activity was standardized by the β-galactosidase activity to control for transfection efficiency and general effects on transcription, and in most experiments further normalized for the transactivation observed in cells expressing Gal4 or LexA alone. Values shown are averages of transactivation assays carried out in duplicate, and repeated at least three times for each cell type and constructs. Most constructs were assayed in three or four cell lines, but usually only representative results for one cell line are shown. To confirm expression of transfected proteins and secretase cleavage of the various APP constructs, transfected cells were also analyzed by immunoblotting using antibodies to the respective proteins and/or antibodies to the epitope tags attached to the proteins.
1.2 Amounts of DNA Used
1.2.1. APP-Gal4VP16 Assays Plasmids used in the following amounts: a. pG5E1B-luc (HEK293 cells, HeLa cells, and COS cells=0.3–0.5 µg DNA; PC12 cells=1.0 µg); b. pCMV-LacZ (HEK293 cells, HeLa cells, and COS cells=0.05 µg DNA; PC12 cells=0.5 µg DNA); c. pMst (Gal4), pMst-GV-APP (APP-GV), pMst-GV (GV), pMst-GV-APPct (APPct-GV), pMst-APPct (APPct-Gal4), pMst-GV-APP* (APP*-GV), pMst-GV-APPγ* (APPγ*-GV), pMst-APPct* (APPct*-Gal4), pMst-GV-APPα (APPα-GV), pMst-GV-NRX (NRX-GV), pMst-GV-NA (NRXe-GV-APPc), pMst-GV-AN (APPe-GV-NRXc) (HEK293, HeLa, and COS cells=0.1–0.3 µg DNA; PC12 cells=1.0 µg DNA). d. pcDNA3.1-PS2D366A, pCMV-Mint1, or pCMV5-Fe65 (HEK293, HeLa, and COS cells= 0.1–0.3 µg DNA; PC12 cells=0.5 µg DNA).

1.2.2. APP-Gal4 and APP-LexA Assays With and Without Various Fe65 and Mint1 Constructs For transactivation by APP-Gal4 and APP-LexA constructs, cells were cotransfected with: a. pG5E1B-luc (Gal4 reporter plasmid) or pL8G5-luc (LexA-reporter plasmid) (HEK293 cells, HeLa cells, and COS cells=0.3 μg DNA; PC12 cells=1.0 μg); b. pCMV-LacZ (β-galactosidase control plasmid. HEK293 cells, HeLa cells, and COS cells= 0.05 μg DNA; PC12 cells=0.2–0.5 μg DNA); c. pMst (Gal4), pMst-APP (APP-Gal4), pMst-APP* (APP*-Gal4), pMst-APPγ (APPγ-Gal4), pMst-APPγ* (APPγ*-Gal4), pMst-AN-APPc32 (APP-G-NRX-APPc32), pMst-AN (APPe-G-NRXc), pML (LexA), pML-APP (APP-LexA), pML-APP* (APP*-LexA), pML-APPct (APPct-LexA), pML-APPct* (APPct*-LexA) (HEK293 cells, HeLa cells, and COS cells= 0.3–0.5 μg DNA; PC12 cells=1.0–1.5 μg); and d. pCMV-Mint1 (mint1) or pCMV5-Fe65 (Fe65) (HEK293 cells, HeLa cells, and COS cells=0.3–0.5 μg DNA; PC12 cells= 1.0–1.5 μg) where indicated.

For transactivation assays of Fe65 mutants, cells were cotransfected with: a. pG5E1B-luc (Gal4 reporter plasmid) or pL8G5-luc (LexA-reporter plasmid); b. pCMV-LacZ (β-galactosidase control plasmid; c. pMst (Gal4), pMst-APP (APP-Gal4), pML (LexA), or pML-APP (APP-LexA); and d. pCMV5-Fe65 (Fe65), pCMVMyc-Fe65(128–711) (Fe65(128–711)), pCMVMyc-Fe65(242–711) (Fe65(242–711)), pCMVMyc-Fe65(287–711) (Fe65(287–711)), pCMV5-Fe65(1–553) (Fe65ΔPTB2), pCMVMyc-Fe65ΔPTB1 (Fe65ΔPTB1), pCMV5-Fe65mW1 (Fe65mW1), pCMV5-Fe65mW2 (Fe65mW2), pCMV5-Fe65mW3 (Fe65mW3), pCMV5-Fe65mW4 (Fe65mW4), or pCMV5-Fe65mW5 (Fe65mW5) where indicated. a. and b.: amounts of DNA same as under 1.21. c. and d.:0.3–0.5 μg DNA for COS, HeLa, and HEK293 cells; 1.0–1.5 μg DNA for PC12 Cells.

1.2.3. Gal4-Tip60 Assays

For transactivation assays of Gal4-Tip60, COS and HEK293 cells were cotransfected with: a. pG5E1B-luc (Gal4 reporter plasmid, 0.3 μg DNA); b. pCMV-LacZ (β-galactosidase control plasmid, 0.05 μg DNA); c. pMst (Gal4); pM-Tip60 (rat Gal4-Tip60 β residues 63–454); pM-Tip60* (mutant rat Gal4-Tip60 β residues 63–454); pM-hTip60 (full-length wild type human Gal4-Tip60 β); or pM-hTip60* (full-length mutant human Gal4-Tip60 β) (0.4 μg DNA) d. pCMV5-Fe65 (Fe65), pCMVMyc-Fe65 (242–711) (Fe65(242–711)), pCMV5-Fe65(1–553) (Fe65ΔPTB2), or pCMV5-Fe65mW4 (Fe65mW4) (0.3 μg DNA) where indicated; and e. pCMV5-APP (human APP695) or pCMV5-APP* (mutant human APP695) (0.3 μg DNA). All transfections contained one of the plasmids listed in a–c, whereas d and e were variable.

2. Yeast Two-hybrid Screens for APP- and Fe65-binding Proteins

2.1 APP Screens

Bait: pBTM116-APP

Yeast strain: L40

Library: P8 rat brain library constructed in prey vector pVP16-3.

Screening condition: 250 ml mid-log phase yeasts harboring the bait vector pBTM116-APP were transformed with 125 μg of P8 rat brain library plasmids, and plated on CSM-Trp-Leu-His plates supplemented with 5 mM 3-amino-1,2,4-triazole. $2 \times 10^7$ total transformants were obtained. Around 250 positives appeared after 3 days incubation at 30° C. 80 positives were recovered and identified by sequencing or Southern blotting. Among them, 72 are Fe65 and one is Fe65-like protein 2 (Fe65LP2).

| Summary of Fe65 prey clones that were sequenced | | | |
|---|---|---|---|
| Prey Clones | Insert Size (kb) | Residues | Extra Residues |
| P29[a] | 3.1 | 1–711 | 43 |
| P50, P64, P65, P69 | 2.9 | 1–711 | 43 |
| P42 | 3.0 | 48–711 | 0 |
| P60[a] | 2.6 | 128–711 | 0 |
| P6[a], P7, P18 | 1.9 | 242–711 | 8 |
| P57 | 2.3 | 242–711 | 50 |
| P19, P25[b] | 1.0 | 242–? | 21 |
| P15, P27[a] | 1.6 | 287–711 | 0 |
| P21 | 1.5 | 301–711 | 0 |
| P4, P22 | 1.4 | 313–711 | 0 |
| P9, P16, P17 | 1.9 | 321–711 | 0 |
| P39 | 1.4 | 339–711 | 0 |

[a]P29, P60, P6, P27 were used to generate pCMV5-Fe65, pCMVMyc-Fe65 (128–711), pCMVMycFe65(242–711), and pCMVMyc-Fe65(287–711), respectively.
[b]P25 insert (1.0 kb) was used as Southern blotting probe to identify the rest of the recovered prey clones.

2.2 Fe65 Screens

Bait: pLexN-Fe65(287–711)

Yeast strain: L40

Library: P8 rat brain library constructed in prey vector pVP16-3.

Screening condition: 250 ml mid-log phase yeasts harboring the bait vector pLexN-Fe65(287-711) were transformed with 125 μg of P8 rat brain library plasmids, and plated on CSM-Trp-Leu-His plates supplemented with 25 mM 3-amino-1,2,4-triazole. $7 \times 10^7$ total transformants were obtained, and ~300 positives selected after 3 days incubation at 30° C.

Summary of prey clones that were sequenced: Tip60 β (residues 63–454)=8 clones; APLP1=9 clones.

3. Quantitative Yeast Two-hybrid Assays

For quantitative measurements of yeast two-hybrid interactions, various bait and prey plasmids were co-transfected into yeast strain L40 and plated on CSM-Trp-Leu (Bio101) plates. Single colonies from the CSM-Trp-Leu plates were cultured in CSM-Trp-Leu liquid medium after 3 days, and re-inoculated into YPAD medium at $OD_{600}$=0.3 on the following day. When the yeast cultures reached mid-log phase ($OD_{600}$=0.6–1.0), cells were collected by centrifugation, washed in Z buffer (16.1 g/l $Na_2HPO_4.7H_2O$, 5.5 g/l $NaH_2PO_4.H_2O$, 0.75 g/l KCl, 0.246 g/l $MgSO_4.7H_2O$ pH 7.0), and resuspended in 100 μl Z buffer. Cells were lysed by three freeze-thawing cycles, 0.8 ml reaction solution (0.5 g/l ONPG and 0.024% β-mercaptoethanol in Z buffer) was added, and reactions were stopped with 0.4 ml 1M $Na_2CO_3$ at the appropriate time points depending on color development. After centrifugation (14,000×g for 10 min), $OD_{420}$ was measured, and the relative β-galactosidase activity was calculated as $1000 \times OD_{420}/(min \times vol.\ yeast\ in\ ml \times OD_{600})$.

| | | | APP & Fe65 | | | | | |
|---|---|---|---|---|---|---|---|---|
| # | Bait | Prey | OD$_{600}$ | Time (min) | OD$_{420}$ | β-gal unit | Mean | S.D. |
| 1 | APPct | P29(Fe65 1–711) | 0.899 | 15 | 5.025 | 372.6363 | 423.8138 | 48.30529 |
| | | | 0.764 | 15 | 4.93 | 430.192 | | |
| | | | 0.685 | 15 | 4.815 | 468.6131 | | |
| 2 | APPct | Fe65mW5 | 0.657 | 15 | 4.895 | 496.7022 | 449.4991 | 71.701238 |
| | | | 0.68 | 15 | 4.945 | 484.8039 | | |
| | | | 0.822 | 15 | 4.525 | 366.9911 | | |
| 3 | APPct | vector | 0.813 | 15 | 0.004 | 0.328003 | 0.370065 | 0.0425321 |
| | | | 0.903 | 15 | 0.005 | 0.36914 | | |
| | | | 0.807 | 15 | 0.005 | 0.413052 | | |
| 4 | APPct* | P29(Fe65 1–711) | 0.776 | 15 | 0.005 | 0.429553 | 0.506697 | 0.0674611 |
| | | | 0.601 | 15 | 0.005 | 0.554631 | | |
| | | | 0.622 | 15 | 0.005 | 0.535906 | | |
| 5 | APPct* | Fe65mW5 | 0.631 | 15 | 0.004 | 0.42261 | 0.44523 | 0.0467628 |
| | | | 0.644 | 15 | 0.004 | 0.414079 | | |
| | | | 0.668 | 15 | 0.005 | 0.499002 | | |

[a]APPct and P29(Fe65 1–711) are bait and prey clones described in the section on the Yeast two-hybrid screen for APP-binding proteins.
[b]APPct* was expressed from pBTM116-APP*, which was generated by QuickChange site-directed mutagenesis kit (Stratagene, LaJolla, CA) to mutate 684NPTY to 684NATA with pBTM116-APP as the template.
[c]Fe65mW5 was expressed from pVP16-3-Fe65mW5, which encodes full-length rat Fe65 (1–711 residues) with Y270A, Y271A, W272A, W281F, and P284A mutations.

| | | | Fe65 & LBP-1c | | | | | |
|---|---|---|---|---|---|---|---|---|
| # | Bait | Prey | OD$_{600}$ | Time (min) | OD$_{420}$ | β-gal unit | Mean | S.D. |
| 1 | Fe65(287–711) | LBP-1c | 0.747 | 60 | 0.037 | 0.825524 | 0.772376 | 0.1010779 |
| | | | 0.737 | 60 | 0.029 | 0.655812 | | |
| | | | 0.678 | 60 | 0.034 | 0.835792 | | |
| 2 | Fe65(287–531) | LBP-1c | 0.686 | 60 | 0.167 | 4.057337 | 4.438847 | 0.3744772 |
| | | | 0.704 | 60 | 0.203 | 4.805871 | | |
| | | | 0.625 | 60 | 0.167 | 4.453333 | | |
| 3 | Fe65(287–711) | vector | 0.709 | 60 | 0.006 | 0.141044 | 0.15965 | 0.0262405 |
| | | | 0.703 | 60 | 0.008 | 0.189663 | | |
| | | | 0.787 | 60 | 0.007 | 0.148242 | | |
| 4 | Fe65(287–531) | vector | 0.725 | 60 | 0.022 | 0.505747 | 0.5543 | 0.0714302 |
| | | | 0.681 | 60 | 0.026 | 0.636319 | | |
| | | | 0.672 | 60 | 0.021 | 0.520833 | | |
| 5 | Lamin | LBP-1c | 0.626 | 60 | 0.017 | 0.452609 | 0.721477 | 0.3382954 |
| | | | 0.819 | 60 | 0.03 | 0.610501 | | |
| | | | 0.454 | 60 | 0.03 | 1.101322 | | | a. Fe65(287–711) and Fe65(287–531) were expressed from pLexN-Fe65(287–711) and pLexN-Fe65(287–531), respectively. Lamin was expressed from pBTM116-Lamin.
b. LBP-1c was expressed from pVP16-3-LBP-1c, which encodes full-length human LBP-1c (1–450 residues). References: Z. Bing, S. A. G. Reddy, Y. Ren, J. Qin, and W. S. L. Liao (1999) J. Biol. Chem. 274, 24649–24656. N. Zambrano, G. Minopoli, P. de Candia, and T. Russo (1998) J. Biol. Chem. 273, 20128–20133.

| | | | Fe65 & hTip60 | | | | | |
|---|---|---|---|---|---|---|---|---|
| # | Bait | Prey | OD$_{600}$ | Time (min) | OD$_{420}$ | β-gal unit | Mean | S.D. |
| 1 | Fe65(287–711) | hTip60 | 0.806 | 15 | 4.905 | 405.7072 | 431.7927 | 45.395309 |
| | | | 0.818 | 15 | 4.975 | 405.4605 | | |
| | | | 0.665 | 15 | 4.83 | 484.2105 | | |
| 2 | Fe65(287–531) | hTip60 | 0.695 | 15 | 3.895 | 373.6211 | 391.1748 | 52.914479 |
| | | | 0.774 | 15 | 4.055 | 349.2679 | | |
| | | | 0.682 | 15 | 4.61 | 450.6354 | | |
| 3 | Fe65(287–711) | vector | 0.709 | 60 | 0.006 | 0.141044 | 0.15965 | 0.0262405 |
| | | | 0.703 | 60 | 0.008 | 0.189663 | | |
| | | | 0.787 | 60 | 0.007 | 0.148242 | | |
| 4 | Fe65(287–531) | vector | 0.725 | 60 | 0.022 | 0.505747 | 0.5543 | 0.0714302 |
| | | | 0.681 | 60 | 0.026 | 0.636319 | | |
| | | | 0.672 | 60 | 0.021 | 0.520833 | | |

-continued

Fe65 & hTip60

| # | Bait | Prey | OD$_{600}$ | Time (min) | OD$_{420}$ | β-gal unit | Mean | S.D. |
|---|------|------|-----|-----|-----|----------|----------|-----------|
| 5 | Lamin | hTip60 | 0.594 | 15 | 0.011 | 1.234568 | 1.751572 | 0.5012274 |
|   |       |        | 0.635 | 15 | 0.017 | 1.784777 |          |           |
|   |       |        | 0.507 | 15 | 0.017 | 2.235371 |          |           | a. Fe65(287–711) and Fe65(287–531) were expressed from pLexN-Fe65(287–711) and pLexN-Fe65(287–531), respectively. Lamin was expressed from pBTM116-Lamin.
b. hTip60 was expressed from pVP16-3-hTip60 which encodes full-length human Tip60β (residues 1–461).
Reference: Qitao Ran and Olivia M. Pereira-Smith (2000) Gene 258, 141–146.

4. Plasmid List
4.1 Standard Plasmids pCMV-LacZ: Transfection control plasmid encoding bacterial β-galactosidase under control of the CMV promoter.

pG5E1B-luc: Gal4 reporter plasmid (Lillie, J. W., and M. R. Green. 1989. Transcription activation by the adenovirus E1 a protein. Nature (London) 338:39–44) in which luciferase mRNA is driven by five copies of Gal4 UAS.

pL8G5-luc: LexA reporter plasmid in which luciferase mRNA is driven by eight copies of the LexA binding site and five copies of Gal UAS. (Hollenberg, S. M., Sternglanz, R., Cheng, P. F., and Weintraub H. 1995. Identification of a new family of tissue-specific basic Helix-Loop-Helix proteins with a two-hybrid system. Mol. Cell. Biol. 15:3813–3822).

pMst: Gal4 expression vector driven by the SV40 promoter derived from pM (Clontech, Palo Alto, Calif.) by mutating the stop codon before the Gal4 DNA-binding domain.

pMst-GV: Gal4 VP16 (GV) expression vector generated by cloning the VP16 activation domain (residues 413–490) into the EcoRI/BamHI sites of pMst (linker sequence between Gal4 and VP16: QLTVSPEFAPPTD; SEQ ID NO:1).

pML: LexA expression vector generated by replacing the NheI/EcoRI fragment of pM (Clontech) with the PCR amplified LexA-coding sequence.

4.2 APP Plasmids
4.2.1. Mammalian Expression Plasmids pMst-GV-APPct, encodes APPct-GV generated by cloning the cytoplasmic tail of human APP695 (APPct, residues 652–695) into the BamHI/SalI sites of pMst-GV (linker sequence between GV and APPct=DEYGGGIPPGQYTSI; SEQ ID NO:2).

pMst-GV-APPct*, encodes APPct*-GV with point mutations in the cytoplasmic tail of APP (residues 684–687; wild type sequence=NPTY; SEQ ID NO:12; mutant sequence=NATA; SEQ ID NO:13). Generated by QuickChange site-directed mutagenesis (Stratagene) with pMst-GV-APPct as template.

pMst-GV-APP encodes APP-GV. Generated by cloning a PCR fragment encoding residues 1–651 of human APP695 into the NheI site of pMst-GV-APPct (linker sequence between APPe and GV=MLKKKPLASSRMKLLS; SEQ ID NO:3).

pMst-GV-APP*, encodes APP-GV with point mutations in the cytoplasmic tail of APP (residues 684–687; wild type sequence=NPTY; SEQ ID NO:12; mutant sequence=NATA; SEQ ID NO:13). Generated by QuickChange site-directed mutagenesis (Stratagene) with pMst-GV-APP as the template.

pMst-GV-APPγ, encodes APPγ-GV containing an N-terminal methionine followed by residues 639–651 of human APP695, Gal4-VP16, and residues 652–695 of APP695. Obtained by inserting the PCR-amplified residues 639–651 into the BglII/NheI sites of pMst-GV-APPct (linker sequence between TMR of APP and Gal4=MLKKKPLASSRMKLLS; SEQ ID NO:3).

pMst-GV-APPγ*, encodes APPγ*-GV corresponding to APPγ-GV with the mutation in the NPTY (SEQ ID NO:12) sequence. Generated by QuickChange site-directed mutagenesis (Stratagene) with pMst-GV-APPγ as the template.

pMst-APPct, encodes APPct-Gal4. Generated by cloning the cytoplasmic tail of human APP695 (APPct, residues 652–695) into the BamHI/SalI sites of pMst (linker sequence between Gal4 and APPct=QLTVSPEFPGIPPGQYTSI; SEQ ID NO:4).

pMst-APPct*, encodes APPct*-Gal4 corresponding to APPct-Gal4 with the NPTY mutation. Generated by cloning the mutant cytoplasmic tail from pMst-GV-APPct* into the BamHI/SalI sites of pMst.

pMst-APP, encodes APP-Gal4. Generated by cloning a PCR fragment containing the extracellular and transmembrane region of human APP695 (APPe, residues 1–651) into the NheI site of pMst-APPct (linker sequence between APPe and Gal4=MLKKKPLASSRMKLLS; SEQ ID NO:3).

pMst-APP*, encodes APP*-Gal4. Obtained as pMst-APP, but cloned into the NheI site of pMst-APPct*.

pMst-APPγ, encodes APPγ-Gal4. Generated by cloning a PCR fragment coding for a methionine and residues 639–651 of human APP695 into the BglII/NheI sites of pMst-APPct (linker sequence between TMR and Gal4 MLKKKPLASSRMKLLS; SEQ ID NO:3).

pMst-APPγ*, encodes APPγ*-Gal4. Obtained as pMst-APPγ, but cloned into pMst-APPct*.

pMst-GV-NRX, encodes NRX-GV. Generated by sequential cloning of PCR fragments coding for the cytoplasmic tail of rat neurexin I (βNRXct, residues 414–468) and the extracellular and transmembrane regions (NRXe, residues 1–417) into the BamHI/SalI and the NheI sites, respectively, of pMst-GV (linker sequences between NRXe and Gal4=MYKYRTLASSRMKLLS; SEQ ID NO:5 and between VP16 and NRXct=DEYGGGIPPGYKYRN; SEQ ID NO:6).

pMst-GV-NA, encodes NRXe-GV-APPc. Generated by cloning a PCR fragment corresponding to NRXe into the NheI site of pMst-GV-APPct (linker sequence between NRXe and Gal4=MYKYRTLASSRMKLLS; SEQ ID NO:5).

pMst-AN encodes APPe-G-NRXc. Generated as pMst-GV-AN, but into pMst (linker sequences between APPe and Gal4=MLKKKPLASSRMKLLS; SEQ ID NO:3, and between Gal4 and NRXct=QLTVSPEFPGIPPGYKYRN; SEQ ID NO:7.

pMst-AN encodes APPe-G-NRXc. Generated as pMst-GV-AN, but into pMst (linker sequences between APPe and Gal4=MLKKKPLASSRMKLLS; SEQ ID NO:3, and between Gal4 and NRXct=QLTVSPEFPGIPPGYKYRN; SEQ ID NO:7.

pMst-AN-AYPc32, encodes APP-G-NRX-APPc32. Generated from pMst-AN by inserting a PCR fragment encoding the C-terminal 32 residues of human APP695 (APPc32) into the rat neurexin I cytoplasmic tail (NRXct) between residue 425 and 427, with V426 deleted during the cloning (linker sequences between APPc32 and NRXct= EGSYHIDDAAVT; SEQ ID NO:8, and between APPc32 and NRXct=EQMQNIDESRLN; SEQ ID NO:9.

pML-APPct, encodes APPct-LexA. Generated by replacing the Gal4 sequence (the NheI/EcoRI fragment) in pMst-APPct with the LexA-sequence (linker sequence between LexA and APPct=NGDWLEFPGIPPGQYTSI; SEQ ID NO:10).

pML-APPct*, encodes APPct*-LexA. Generated as pML-APPct in pMst-APPct*.

pML-APP, encodes APP-LexA. Generated by cloning the extracellular and transmembrane region of human APP695 (APPe, residues 1–651) into the NheI site of pML-APPct (linker sequence between APPe and LexA= MLKKKPLAKMKALT; SEQ ID NO:11).

pML-APP*, encodes APP*-LexA. Generated as pML-APP with pML-APPct*.

pCMV5-APP, encodes full-length human APP695 inserted into the blunted-EcoRI/XbaI sites of pCMV5.

pCMV5-APP*, encodes full length human APP695 containing point mutations in the cytoplasmic NPTY sequence. Generated by QuickChange site-directed mutagenesis (Stratagene) with pCMV5-APP.

4.2.2. Yeast Two-hybrid Plasmids pBTM116-APP, encodes residues 648–695 of human APP695 cloned into the BamHI/SalI sites of the yeast two-hybrid bait vector pBTM116 using a PCR fragment.

pBTM116-APP*=pBTM116-APP in which the codons encoding the NPTY sequence in the APP cytoplasmic tail were mutated to NATA using QuickChange site-directed mutagenesis (Stratagene).

4.3 Fe65 Plasmids 4.3.1. Mammalian Expression Plasmids pCMV5-Fe65: encodes full-length rat Fe65 (711 residues). Constructed by sub-cloning the 3 kb SalI fragment from the yeast two-hybrid prey clone #P29 into the SalI site of pCMV5.

pCMVMyc-Fe65(128–711): encodes residues 128–711 of Fe65. Generated by cloning the blunt-ended fragment from the rat Fe65 cDNA into the blunted EcoRI site in pCMV-Myc.

pCMVMyc-Fe65(242–711): encodes residues 242–711 of Fe65. Generated by cloning the blunt-ended fragment from the rat Fe65 cDNA into the blunted EcoRI site in pCMV-Myc.

pCMVMyc-Fe65(287–711): encodes residues 287–711 of Fe65. Generated by cloning the blunt-ended fragment from the rat Fe65 cDNA into the blunted EcoRI site in pCMV-Myc.

pCMV5-Fe65(1–553): encodes Fe65 PTB2 which lacks residues 554–711 of Fe65. Generated by introducing a stop codon into pCMV5-Fe65 after residue 553 with the Quick-Change site directed mutagenesis kit (Stratagene).

pCMVMyc-Fe65 ΔPTB 1: encodes Fe65 ΔPTB1 which lacks residues 314–440. Generated by sequentially cloning the PCR fragments encoding residues 441–711 and residues 1–313 of rat Fe65 into the ClaI and MluI sites, respectively, of pCMVMyc.

pCMV5-Fe65mW1: encodes Fe65mW1 point mutant in carrying substitutions W281F and P284A. Generated by QuickChange site directed mutagenesis (Stratagene) with pCMV5-Fe65 as template.

pCMV5-Fe65mW2: encodes Fe65mW2 point mutant in carrying substitution W260F. Generated by QuickChange site directed mutagenesis (Stratagene) with pCMV5-Fe65 as template.

pCMV5-Fe65mW3: encodes Fe65mW3 point mutant in carrying substitutions W260F, W281F and P284A. Generated by QuickChange site directed mutagenesis (Stratagene) with pCMV5-Fe65mW1 as template.

pCMV5-Fe65mW4: encodes Fe65mW4 point mutant in carrying substitutions Y270A, Y271A, and W272A. The insert (2.1 kb) can be cut out by HindIII+SalI double digestion.

pCMV5-Fe65mW5: encodes Fe65mW4 point mutant in carrying substitutions Y270A, Y271A, W272A, W281F, and P284A. The insert (2.1 kb) can be cut out by HindIII+SalI double digestion.

pcDNA3.1-N-HA-Fe65: encodes full-length rat Fe65 preceded by a hemagglutinin (HA) epitope. Obtained by sub-cloning the rat Fe65 cDNA into the blunted-EcoRI/XbaI sites of pcDNA3.1-N-HA.

4.3.2. Yeast Two-hybrid Plasmids pLexN-Fe65(287–711), encodes residues 287–711 of Fe65 in the SalI/blunted-PstI sites in pLexN.

pLexN-Fe65(287–531), encodes residues 287–531 of Fe65 in the BamHI/blunted-SalI sites in pLexN. Insert (740 bp) can be cut out by BamHI+PstI double digestion.

pVP16-3-Fe65mW5, encodes the mW5 mutant of Fe65 (see pCMV vectors above). Was generated by cloning the blunted 2.1 kb HindIII/XbaI fragment from pCMV5-Fe65mW5 into the blunted-NotI/XbaI sites of the yeast prey vector pVP16-3. The insert can be cut out by SalI.

4.4 Tip60 Plasmids 4.4.1. pCMV Expression Plasmids pCMVMyc-Tip60(63–454), encodes residues 63–454 of rat Tip60β. Generated by cloning the 1.3 kb EcoRI fragment from yeast two-hybrid prey clone #B36 into the EcoRI site of pCMVMyc.

pCMVMyc-Tip60(63–454)*, encodes residues 63–454 of rat Tip60β with a mutation in residues 257–260 (sequences: wild-type=NKSY; SEQ ID NO:12; mutant=NASA; SEQ ID NO:14). Generated by QuickChange site directed mutagenesis kit (Stratagene) with pCMVMyc-Tip60(63–454) as template.

pM-Tip60 encodes rat Tip60β residues 63–454 preceded by the Gal4 DNA-binding domain. Generated by subcloning the 1.3 kb BamHI/XbaI fragment from prey clone #36 into the BamHI/XbaI sites of pM.

pM-Tip60* encodes the same protein as pM-Tip60 with the inactivating mutation in residues 257–260. Generated by cloning the 1.3 kb BamHI/XbaI fragment from pVP16-3-Tip60* into the BamHI/XbaI sites of pM.

pCMVMyc-hTip60 encodes myc-tagged full-length human Tip60β. Obtained by subcloning the insert of EST IMAGE clone 2901054 into the MluI/XbaI sites of pCMV-Myc.

pM-hTip60 encodes full-length human Tip60β preceded by the Gal4-DNA binding domain. Obtained by cloning the blunted 1.6 kb EcoRI/NotI fragment from EST clone 2901054 into the blunted EcoRI site of pM. Insert can be cut out by SalI.

pM-hTip60*, same as pM-hTip60 but with the inactivating mutation in residues 257–260. Generated by Quick-Change site directed mutagenesis (Stratagene) with pM-hTip60 as template.

4.5 Yeast Two-hybrid Plasmids

Prey clone #B36 in pVP16-3; identified in yeast two-hybrid screens with pLexN-Fe65(287–711) as the bait in a P8 rat brain library. B36 encodes rat Tip60β corresponding to residues 63–454 of human Tip60, with a single amino acid change between human and rat sequences.

pVP16-3-Tip60* encoding mutant rat Tip60 with the inactivating mutation in residues 257–260 (sequences: wild-type=NKSY; SEQ ID NO:12; mutant=NASA; SEQ ID NO:14). Generated by cloning the EcoRI fragment from pCMVMyc-Tip60(63–454)* into the EcoRI site of yeast prey vector pVP16-3.

pVP16-3-hTip60, full-length human Tip60 cloned into the EcoRI/NotI sites of pVP16-3.

4.6 GST-fusion Protein Plasmids pGEX-KG-Tip60(63–454), residues 63–454 Tip60β fused to GST. Generated by cloning the 1.3 kb EcoRI fragment (1.3 kb) of the yeast two-hybrid prey clone B36 into the EcoRI site of pGEX-KG.

pGEX-KG-Tip60(63–454)*, encodes residues 63–454 Tip60β fused to GST. Generated as pGEX-KG-Tip60(63–454), but from pVP16-3-Tip60(63–454)*.

5. Miscellaneous Plasmids

5.1 pCMV Expression Plasmids pCMV5-Mint-1: rat Mint1 cloned into the EcoRI site of pCMV5 (Okamoto, M. and Südhof, T. C. (1997) *J. Biol. Chem.* 272, 31459–31464.)

pCS2+MT-SEF: Myc-tagged full-length human LBP-1c (1–450 residues) was expressed from control of the CMV promoter (gift from Dr. W. S. L. Liao, University of Texas MD Anderson Cancer Center, Houston Tex.; reference: Z. Bing, S. A. G. Reddy, Y. Ren, J. Qin, and W. S. L. Liao (1999) *J. Biol. Chem.* 274, 24649–24656.)

pcDNA3.1-PS2D366A (kind gift of Dr. C. Haass, Munich): encodes a dominant negative mutant of human presenilin 2 in pcDNA3.1.

5.2 Yeast Two-hybrid Plasmids pVP16-3-LBP-1c, encodes full-length human LBP-1c. Generated by cloning the blunted 1.4 kb XhoI fragment from pCS2+MT-SEF into the blunted NotI site of the yeast prey vector pVP16-3. Insert can by cut out by XhoI.

6. Transfections, Transactivation Assays, and Yeast Two Hybrid Screens

PC12, COS, HeLa, and HEK293 cells were co-transfected at 50–80% confluency in 6-well plates using Fugene6 (Roche), and 3–5 plasmids (0.1–1.0 μg DNA/well depending on cell types; see plasmid list hereinabove for description of all constructs). All transfections included a. Gal4 (pG5E1B-luc) or LexA (pL8G5-luc) reporter plasmids; b. constitutively expressed β-galactosidase expression plasmid (pCMV-LacZ) to control for transfection efficiency; and c. the Gal4- or LexA-fusion protein vectors. Cells were harvested 48 hr post-transfection in 0.2 ml/well reporter lysis buffer (Promega), and their luciferase and β-galactosidase activities were determined with the Promega luciferase assay kit and the O-nitrophenyl-D-galacto-pyranoside method, respectively. The luciferase activity was standardized by the β-galactosidase activity to control for transfection efficiency and general effects on transcription, and in most experiments normalized for the transactivation observed in cells expressing Gal4 or LexA alone. Values shown are averages of transactivation assays carried out in duplicate, and repeated at least three times for each cell type and constructs. Most constructs were assayed in three or four cell lines, but usually only representative results for one cell line are shown. To confirm expression of transfected proteins and secretase cleavage of the various APP constructs, transfected cells were also analyzed by immununoblotting using antibodies to the respective proteins and/or antibodies to the epitope tags attached to the proteins.

For assays of the transactivation by Gal4•VP16 constructs, cells were cotransfected with a. pG5E1B-luc (Gal4 reporter plasmid); b. pCMV-LacZ (β-galactosidase control plasmid); c. pMst (Gal4), pMst-GV-APP (APP-GV), pMst-GV (GV), pMst-GV-APPct (APPct-GV), pMst-APPct (APPct-Gal4), pMst-GV-APP* (APP*-GV), pMst-GV-APPct* (APPct*-GV), pMst-APPct* (APPct*-Gal4), pMst-GV-APPγ (APPγ-GV), pMst-GV-NRX (NRX-GV), pMst-GV-NA (NRXe-GV-APPc), or pMst-GV-AN; and d. pcDNA3.1-PS2D366A (kind gift of Dr. C. Haass, Munich), pCMV-Mint1; or pCMV5-Fe65 where indicated.

A yeast two-hybrid cDNA library in pVP16-3 was screened with pBTM116-APP encoding the cytoplasmic tail of human APP$_{695}$ as described (Vojtek et al. (1993) Cell 74, 205–214; Okamoto et al. (1997) J. Biol. Chem. 272: 31459–31464). Of 80 positive clones, 72 encoded Fe65 and one Fe65-like protein. The full-length rat Fe65 sequence has been submitted to GenBank (acc.# AF333983). Interactions of all proteins including mutants of Fe65 were quantified using liquid β-galactosidase assays on yeast strains harboring various bait and prey clones (see Example 1).

For transactivation by APP-Gal4 and APP-LexA constructs, cells were cotransfected with: a. pG5E1B-luc (Gal4 reporter plasmid) or pL8G5-luc (LexA-reporter plasmid); b. pCMV-LacZ (β-galactosidase control plasmid); c. pMst (Gal4), pMst-APP (APP-Gal4), pMst-APP* (APP*-Gal4), pMst-APPγ (APPγ-Gal4), pMst-APPγ* (APPγ*-Gal4), pMst-AN-APPc32 (APP-G-NRX-APPc32), pMst-AN (APPe-G-NRXc), pML (LexA), pML-APP (APP-LexA), pML-APP* (APP*-LexA), pML-APPct (APPct-LexA), pML-APPct* (APPct*-LexA); and d. pCMV-Mint1 (mint1) or pCMV5-Fe65 (Fe65) where indicated. Analyses were performed as described above.

COS7 cells were transfected in 100 mm dishes using DEAE-dextran or Fugene6 (Roche) with single or combinations of expression vectors encoding wild-type and mutant APPct-Gal4, APPγ-Gal4, and APP-Gal4, myc-tagged or HA-tagged wild type or mutant Fe65, and wild type and mutant Tip60 (see above for a description of the expression vectors), and harvested 72 hr after transfection. For the immunoblotting experiments (FIG. 3), cell extracts were immunoblotted with polyclonal antibodies to the C-terminus of APP (U955) or to Fe65, and with monoclonal antibodies to Gal4 (Clontech) or to the myc- or HA-epitope (Santa Cruz). For the immunoprecipitation experiments (FIG. 5), cells were washed twice with cold PBS, harvested in 1 ml lysis buffer (50 mM HEPES-NaOH pH 7.5, 150 mM NaCl, 10% glycerol, 1% IGEPAL CA-630, 1.5 mM MgCl2, 1 mM EGTA, 1 mM DTT, 0.1 g/L PMSF, 10 mg/L Leupeptin, 10 mg/L aprotinin, 1 mg/L pepstatin A), and passed through a 28 gauge needle 5×. Cell extracts were clarified by centrifugation at 20,800×g for 10 min. The supernatants (~1 ml) were incubated with 10 μl of a polyclonal antibody raised against the C-terminus of APP (U955) or monoclonal antibodies to myc-tag (Santa Cruz) for 2 hr at 4° C., 60 μl of a 50% slurry of protein A- or protein G-Sepharose (Phamacia) were added, and the beads were incubated with the reactions for 1 hr at 4° C. on a rotator and then collected by centrifugation. Beads were washed 3× with lysis buffer, resuspended in 0.1 ml SDS-PAGE sample buffer, and 20 μl of the protein solutions were resolved on 10% SDS-PAGE, and detected by immunoblotting with antibodies to APP, Gal4, or the myc-epitope.

For transactivation assays of Fe65 mutants, cells were cotransfected with: a. pG5E1B-luc (Gal4 reporter plasmid) or pL8G5-luc (LexA-reporter plasmid); b. pCMV-LacZ (β-galactosidase control plasmid); c. pMst (Gal4), pMst- APP (APP-Gal4), pML (LexA), or pML-APP (APP-LexA); and d. pCMV5-Fe65 (Fe65), pCMVMyc-Fe65(128–711) (Fe65(128–711)), pCMVMyc-Fe65(242–711) (Fe65 (242–711)), pCMVMyc-Fe65(287–711) (Fe65(287–711)), pCMV5-Fe65(1–553) (Fe65ΔPTB2) pCMVMyc-Fe65ΔPTB1 (Fe65ΔPTB1), pCMV5-Fe65mW1 (Fe65mW1), pCMV5-Fe65mW2 (Fe65mW2), pCMV5-Fe65mW3 (Fe65mW3), pCMV5-Fe65mW4 (Fe65mW4), or pCMV5-Fe65mW5 (Fe65mW5) where indicated. Analyses were performed as described above, and plasmids are described above.

Yeast two-hybrid screens were carried out with a fragment from rat Fe65 (residues 287–711) as described above. Out of 100 clones analyzed, 9 clones encoded APLP1, and 8 clones Tip60 β (residues 63–454 of the insert-minus splice β-variant; submitted to GenBank with acc.# AF333984). The domains of Fe65 that bind to the cytoplasmic tail of APP or to Tip60 were studied by quantitative yeast two-hybrid assays which demonstrated that the first PTB domain of Fe65 is necessary and sufficient for bind to Tip60, and the second PTB domain for binding to APP. For Tip60, both the partial rat cDNA and the full-length human cDNA were analyzed (see FIG. 6A).

GST-pulldowns were performed essentially as described by Hata et al. (1993) Nature 366, 347–351 using purified wild type and mutant rat GST-Tip60β and Fe65 expressed by transfection in COS cells. Extracts from transfected COS cells were preabsorbed with 10 μg GST on glutathione agarose for 2 hr at 4° C., and then incubated for 4 hrs at 4° C. with 10 μg of GST-Tip60, GST-Tip60*, or GST bound to glutathione agarose. Beads were washed 5× in lysis buffer, resuspended in 80 μl SDS-PAGE sample buffer, and 20 μl were analyzed by SDS-PAGE and immunoblotting using antibodies to Fe65 and to the myc epitope. Co-immunoprecipitation experiments of Fe65, APP, and wild-type and mutant rat Tip60β were performed as described above using COS cells co-transfected with the appropriate vectors.

HeLa cells plated on cover glass in a 12-well plate were transfected with pcDNA3.1-N-HA-Fe65 and pCMVMyc-hTip60 (0.25 μg for each plasmid) using Fugene6 (Roche). Two days after transfection, cells were washed twice with PBS, fixed (3.7% formaldehyde for 10 min at room temperature), and blocked and permeabilized in PBS containing 3% BSA, 0.1% IGEPAL CA-630 for 20 min. Cells were then incubated with anti-HA monoclonal antibody (BAbCO Berkeley antibody company) and anti-Myc polyclonal antibody (Upstate Biotechnology) for 1 hr (1:200 dilution in blocking buffer), washed with PBS 3×, and treated with Rhodamine-goat-anti-mouse and FITC-goat-anti-rabbit antibodies (Chemicom) for 1 hr (1:500 dilution in blocking buffer). After 3 washes with PBS and one wash with water, cells were mounted and observed with a confocal microscope.

For transactivation assays of Gal4Tip60, COS and HEK293 cells were cotransfected with: a. pG5E1B-luc (Gal4 reporter plasmid); b. pCMV-LacZ (β-galactosidase control plasmid); c. pMst (Gal4); pM-Tip60 (rat Gal4-Tip60β residues 63–454); pM-Tip60* (mutant rat Gal4-Tip60β (residues 63–454); pM-hTip60 (full-length wild type human Gal4-Tip60β); or pM-hTip60* (full-length mutant human Gal4-Tip60β) d. pCMV5-Fe65 (Fe65), pCMVMyc-Fe65(242–711) (Fe65(242–711)), pCMV5-Fe65(1–553) (Fe65ΔPTB2), or pCMV5-Fe65mW4 (Fe65mW4) where indicated; and e. pCMV5-APP (human APP695) or pCMV5-APP* (mutant human APP695). All transfections contained one of the plasmids listed in a–c, whereas d and e were variable. Analyses were performed as described above.

EXAMPLE 2

Nuclear signaling by the cytoplasmic γ-cleavage product of APP fused to Gal4•VP16. Cleavage of APP produces a C-terminal fragment composed of half of the TMR (10–12 residues) and the cytoplasmic tail (47 residues) (See, e.g. Selkoe (1998) Trends Cell Biol. 8, 447–453). A transcription factor was engineered into the cytoplasmic tail of APP. The inserted transcription factor was Gal4•VP16 which is composed of a yeast DNA-binding protein (Gal4) fused to a powerful viral activator (VP16) (Sadowski et al. (1988) Nature 335, 563–564). When inserted in the cytoplasmic tail of APP, Gal4•VP16 can only act as a transcription factor if APP is cleaved by γ-secretase, and if the resulting product enters the nucleus. Gal4•VP16 was inserted into full-length APP695 at the cytoplasmic boundary of the TMR, the resulting APP-Gal4•VP16 fusion protein was transfected into a variety of cell lines (PC12, HEK293, COS, or HeLa cells), and transactivation of transcription from a co-transfected Gal4-dependent reporter plasmid encoding luciferase was measured. Isolated Gal4•VP16 (without APP) was employed as a positive control, and Gal4 alone (without VP16 and APP) as a negative control. In all experiments, cells were co-transfected with a constitutive β-galactosidase expression plasmid in order to control for transfection efficiency, and verified protein expression by immunoblotting. Transfections and analyses were performed as described in Example 1.

Full-length APP-Gal4•VP16 (APP-GV) transactivated Gal4-dependent transcription much stronger than Gal4 alone in all cell types tested (~500–2,000 fold activation depending on cell type). Surprisingly, full-length APP-Gal4•VP16 was as powerful in activating Gal4-dependent transcription as free Gal4•VP16 (GV) without APP (FIG. 1A #1–3). Immunoblotting revealed that the transfected proteins were expressed well, and that APP-Gal4•VP16 was partly cleaved by α- or β- and γ-secretases in the cells, resulting in stable C-terminal fragments which could be detected by antibodies to Gal4 and to the cytoplasmic tail of APP. A chimeric protein in which Gal4•VP16 was only fused to the cytoplasmic tail of APP without the TMR and extracellular sequences of APP (APPct-GV) was more potent in transactivation than full-length APP-Gal4•VP16, or even Gal4•VP16 alone (~3,000 vs. ~1,000 fold activation; FIG. 1A #5). In contrast, the cytoplasmic APP tail containing only Gal4 without VP16 (APPct-Gal4) was only slightly more active than Gal4 alone (<5 fold activation; FIG. 1A #8). Together these results show that the cytoplasmic tail of APP released by γ-cleavage is competent to enter the nucleus, and may partly activate transcription. Similar results were obtained in all cells tested, and thus are not a unique property of a particular cell line.

To rule out the possibility that transactivation by APP-Gal4•VP16 in transfected cells may be caused by non-specific proteolysis of the APP-Gal4•VP16 fusion protein instead of γ-cleavage, the γ-cleavage product of APP with an inserted Gal4•VP16 module in the cytoplasmic tail (APP γ-GV) was directly expressed, and its ability to activate Gal4-dependent transcription was measured (FIG. 1A #6). Similar to the cytoplasmic tail fragment of APP, the isolated γ-cleavage product was more active in transcription than full-length APP-Gal4•VP16 or Gal4•VP16 alone, confirming that the hydrophobic residues in the γ-cleavage product do not inhibit transactivation.

EXAMPLE 3

Sequence-specificity of transactivation mediated by •APP-Gal4VP16. The cytoplasmic tail of APP contains a conserved NPTY sequence that constitutes a binding site for the PTB-domains of at least three proteins, Fe65, Mints/X11s, and Disabled (Fiore et al. (1995) J. Biol. Chem. 270, 30853–30856; McLoughlin et al. FEBS Lett. 397, 197–200; Borg et al. (1996) Mol. Cell. Biol. 16, 6229–6241). Binding of these proteins to APP could contribute to the transcriptional activation mediated by APP-Gal4•VP16 by influencing γ-cleavage of APP, or by participating in nuclear translocation. This possibility was examined by mutating the NPTY (SEQ ID NO:12) sequence in the cytoplasmic tail of APP to NATA (SEQ ID NO:13). Transactivation assays showed that in all cell types tested, the NPTY-mutants of Gal4•VP16 fusion proteins were as potent as wild type proteins in activating transcription (FIG. 1A #4, 7 & 9), suggesting that the NPTY motif and its binding proteins are not essential for transactivation by the Gal4•P16 module inserted into APP. In agreement with this conclusion, co-transfection of Fe65 did not cause a major change in transactivation by APP-Gal4•VP16.

The specificity of transactivation by Gal4•VP16 inserted into a membrane protein was examined by introducing Gal4•VP16 into the cytoplasmic tail of neurexin 1β as a control protein that is also expressed on the neuronal cell-surface but is not known to be processed by proteolytic cleavage (Ushkaryov et al. (1992) Science 257, 50–56). Neurexin 1β-Gal4•VP16 (NRX-GV) did not exhibit transactivation in contrast to APP-Gal4•VP16 (FIG. 1B, #3 & 10), suggesting that not all cell-surface Gal4•VP16-fusion proteins are competent for transactivation. In these experiments, a dominant negative mutant of presenilin 2 (Steiner et al. (1999) J. Biol. Chem. 274, 28669–28673) was co-transfected with the Gal4•VP16-fusion proteins to test if presenilins are involved. As expected, transactivation by full-length APP-Gal4•VP16 was inhibited by the presenilin 2 mutant, whereas the small amount of residual transactivation observed with neurexin 1β-Gal4•VP16 was insensitive to presenilin 2 (FIG. 1B, #3 & 10).

To determine which APP sequences enable the inserted Gal4•VP16 to activate transcription, chimeric proteins containing different combinations of the extracellular and intracellular sequences of APP and of neurexin 1β were produced. When extracellular sequences and TMR of APP were fused to Gal4•VP16 and to the cytoplasmic tail of neurexin 1β (APPe-GV-NRXc), potent transactivation was observed. In contrast, the reverse fusion protein of the extracellular domain and TMR of neurexin 1β with the cytoplasmic tail of APP (NRXe-GV-APPc) was inactive (FIG. 1B, #11 and 12). Again, presenilin 2 inhibited the chimeric protein containing the extracellular domain of APP but had no effect on the residual transactivation observed with the protein containing the extracellular domain of neurexin 1β, supporting the notion that specific APP-sequences are required for transactivation as studied by this assay.

EXAMPLE 4

Fe65 binding to the cytoplasmic tail of APP stimulates transcription.

To identify co-factors that may be involved in nuclear signaling with the cytoplasmic tail of APP, yeast two-hybrid screens for proteins that bind to the cytoplasmic tail of APP were performed as described in Example 1. Similar to previous screens (26–31), Fe65 was the major interacting protein identified, although it was isolated at an unexpectedly high frequency (90% of all clones).

Figure 2A:
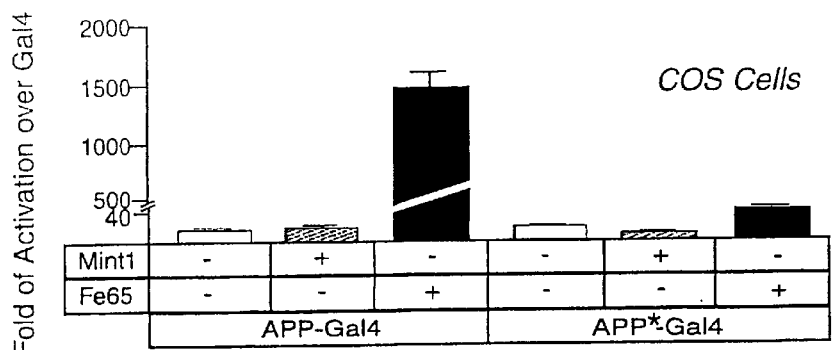
FIGS. 2A–D show results of Gal4-transactivation assays (FIGS. 2A–C) obtained with the constructs depicted (FIG. 2D). All bar diagrams exhibit representative experiments in the cell types identified to the right of the panel.
Figure 2B:
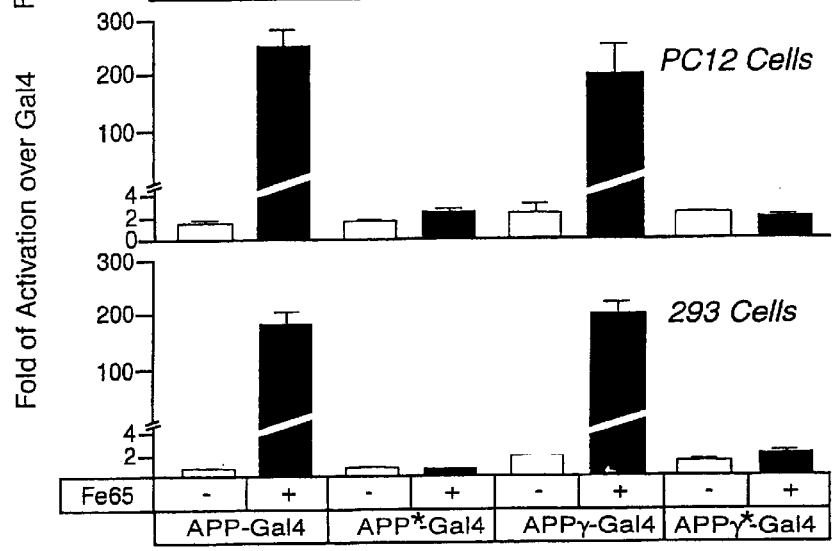
Figure 2C:
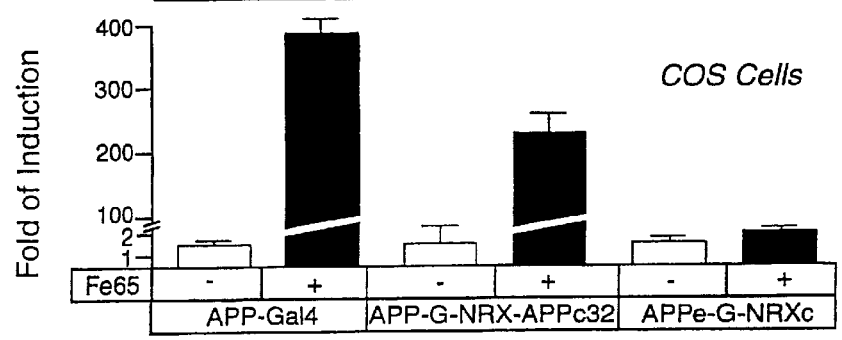
Figure 2D:
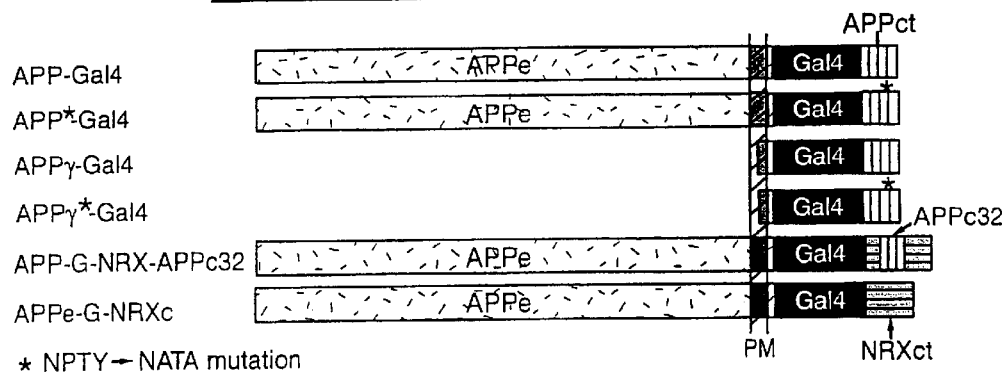

A further assay was performed to determine whether Fe65 represents a co-factor for APP in nuclear signaling. Without Fe65, APP-Gal4 activated Gal4-dependent transcription only weakly (<10 fold). By contrast, co-expression of Fe65 with APP-Gal4 powerfully stimulated transcription (200–2,000 fold depending on the cell type). This was observed in all cell lines tested (PC12, HEK293, COS, or HeLa cells) (FIGS. 2A–2C). As a control, co-expression of mint 1/X11 which also binds to the cytoplasmic tail of APP (See, e.g., Fiore et al. (1995) J. Biol. Chem. 270; 30853–30856), had no major effect on transactivation under these conditions. Neither Fe65 nor mint1/X11 changed the transcription of the control β-galactosidase plasmid co-transfected into all cells.

To examine whether Fe65 still stimulates transactivation when the Fe65-binding site in the cytoplasmic tail of APP (the NPTY sequence) is mutated, yeast two hybrid assays and co-immunoprecipitations were performed as described in Example 1. Replacing the NPTY (SEQ ID NO:12) sequence with NATA (SEQ ID NO:13) abolished Fe65 binding as shown by yeast two-hybrid assays and co-immunoprecipitations (see also FIG. 5 below). In agreement with a direct role for Fe65 in stimulating transactivation by the cytoplasmic tail of APP, the same mutation also abolished the Fe65-dependent stimulation of transcription (FIG. 2A).

The hypothesis that Fe65 binds to the cytoplasmic γ-cleavage product of APP to activate Gal4-dependent transcription in the nucleus was confirmed by the observation that Fe65 powerfully stimulated transactivation by a "pre-cleaved" APP-Gal4 fragment corresponding to the γ-cleavage product (200–2,000 fold stimulation of transactivation depending on cell type; FIG. 2B). The effect of Fe65 depended on the intact Fe65-binding site in the cytoplasmic tail of APP (FIG. 2B). The relative activity of APP-Gal4 co-transfected with Fe65 compares well to that of the potent Gal4•VP16 fusion protein, suggesting that Fe65 is a powerful transcriptional activator. Further evidence for the notion that Fe65 needs to bind to the cytoplasmic APP tail in order to stimulate transcription was obtained with series of chimeric APP/neurexin constructs (FIG. 2C). When the cytoplasmic tail of APP-Gal4 was replaced with the cytoplasmic tail of neurexin 1β, Fe65 did not stimulate transactivation. However, when the 32 amino acid Fe65-binding site from the cytoplasmic tail of APP was transplanted into the middle of the neurexin cytoplasmic tail, powerful stimulation of transcription (>200 fold over Gal4) was observed (FIG. 2C).

Figure 3:
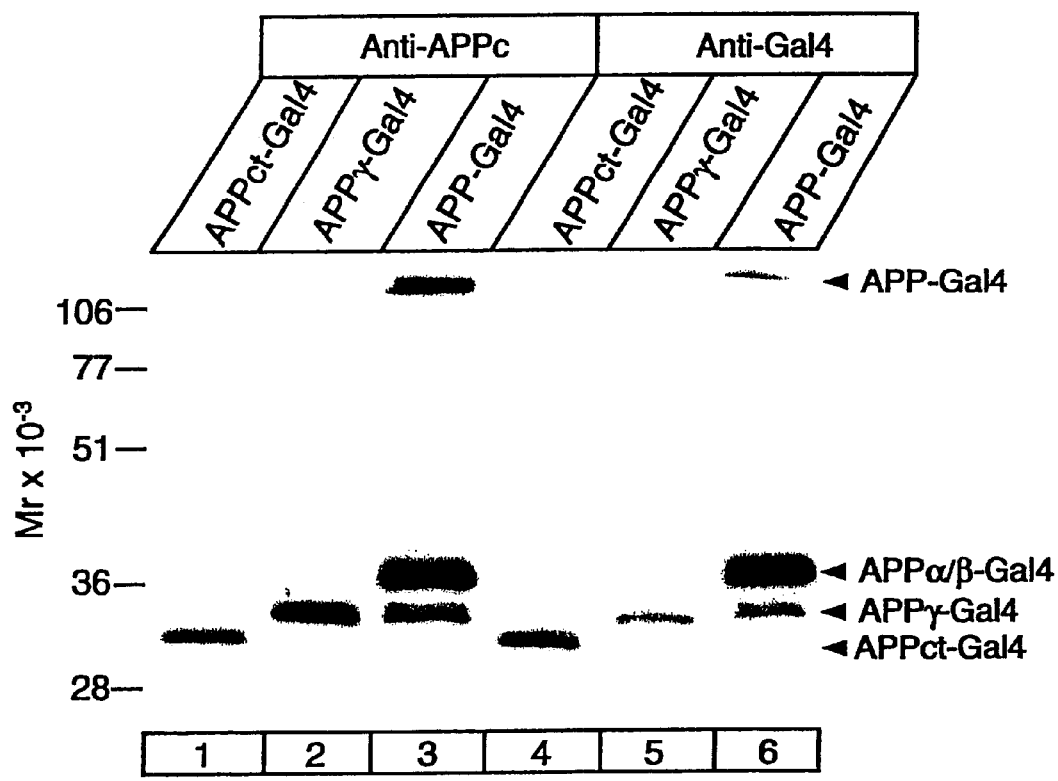
FIG. 3 depicts an immunoblot of COS cells transfected with APP-Gal4 fusion proteins. The positions of full-length APP-Gal4, the α/β- and γ-cleavage products of APP-Gal4 (APP cc/β-Gal4 and APP γ-Gal4, respectively) and the cytoplasmic tail of APP-Gal4 (APPct-Gal4) are indicated on the right. Numbers on the left show positions of molecular weight markers.

To ensure that APP-Gal4 is indeed cleaved at the γ-secretase site in the transfected cells, the size of the APP-Gal4 cleavage products was examined. COS cells were transfected with Gal4-fusion proteins of full-length APP (as test protein), and of the cytoplasmic tail and the γ-cleavage product of APP (as size standards to identify the correct cleavage product) as described above. Immunoblotting of the transfected cells with antibodies to the cytoplasmic tail of APP and to Gal4 detected two major APP cleavage products (FIG. 3). A fragment that was bigger than the γ-cleavage product, tentatively identified as the – or β-secretase product, and a fragment that of precisely the same size as the γ-cleavage product but slightly larger than the cytoplasmic tail protein alone (FIG. 3) were detected. No artifactual cleavage at the boundary of the TMR and the inserted Gal4 protein was detected, while the γ-secretase cleavage product was abundantly produced. Furthermore, analyses of cells co-transfected with Fe65 revealed that Fe65 had no apparent effect on the production of the α- and γ-cleavage products.

EXAMPLE 5

Figure 4A:
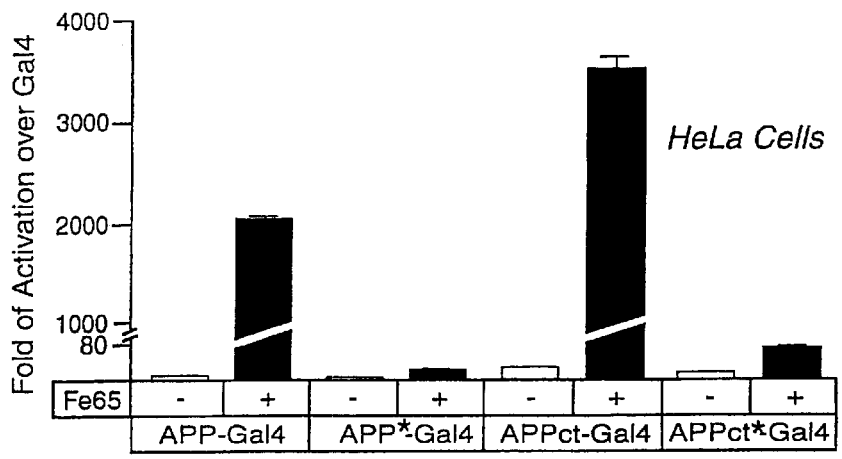
FIGS. 4A–C show transactivation of transcription measured with Gal4-fusion proteins and a Gal4-dependent reporter plasmid (FIG. 4A) as compared with transactivation obtained with LexA-fusion proteins and a LexA-dependent reporter plasmid (FIG. 4B). The structures of the proteins co-expressed with the reporter plasmids and the control β-galactosidase vector are shown in FIG. 4C. Transcriptional activation is expressed as fold increase over transcription obtained with the DNA-binding proteins expressed alone.
Figure 4B:
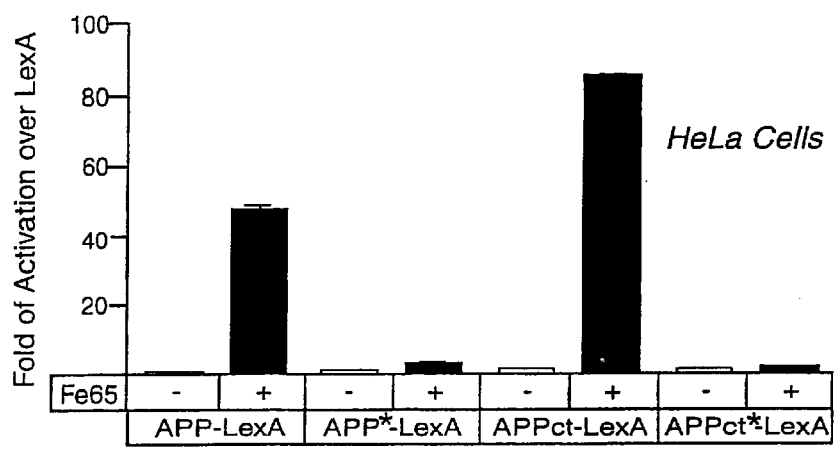
Figure 4C:
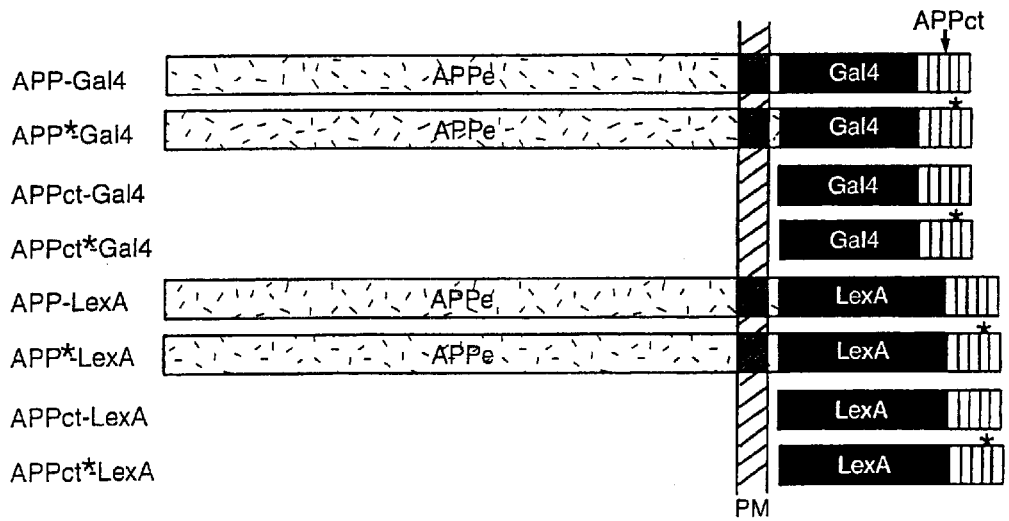

Fe65 stimulates transactivation independent of the DNA binding protein. Gal4 contains an intrinsic nuclear localization signal (Silver et al. (1984) Proc. Natl. Acad. Sci. USA 81, 5951–5955) and theoretically could cause non-specific transcriptional activation that could be unrelated to the normal functions of these proteins. To exclude Gal4-specific artifacts, APP was fused to the bacterial LexA DNA-binding protein (Smith et al. (1988) EMBO J. 7, 3975–3982), and measured Fe65-dependent transactivation with a LexA-dependent luciferase reporter as described in Example 3 (FIG. 4). In the absence of Fe65, APP-LexA did not mediate significant transactivation (FIG. 4B). However, co-transfection of Fe65 strongly stimulated transactivation (40–100 fold). The effect of Fe65 was less pronounced with LexA than with Gal4, possibly because the bacterial LexA DNA-binding domain acting on a bacterial promoter sequence is less optimal for mammalian transcription. Similar to the Gal4 system, however, Fe65 stimulated transactivation both with full-length APP and with the isolated cytoplasmic tail, and stimulation depended on the intact Fe65-binding site in the cytoplasmic tail of APP.

EXAMPLE 6

The WW-domain and both PTB-domains of Fe65 are required for transactivation. Fe65 is a multidomain protein that contains a negatively charged N-terminal sequence with no homology to other proteins, a central WW-domain, and two C-terminal PTB-domains (Ermekova et al. (1998) Adv. Exp. Med. Biol. 446, 161–180; McLoughlin et al. (1998) Biochem. Soc. Trans. 26, 497–500). The WW-domain of Fe65 interacts with the cytoskeletal adaptor protein mena (Ermekova et al. (1997) J. Biol. Chem. 272, 32869–32877). The second PTB-domain of Fe65 (PTB2) binds to the cytoplasmic tails of APP and other cell-surface proteins containing NPxY motifs (Fiore et al. (1995) J. Biol. Chem. 270: 30853–30856). In addition to these cytoplasmic activities, Fe65 has been implicated in nuclear functions. Fe65 is partly localized to the nucleus, its first PTB-domain (PTB1) binds to the transcription factor CP2/LSF/LBP1, and its negatively charged N-terminal sequences stimulates Gal4-dependent transcription (Duilio et al. (1991) Nucleic Acids Res. 19, 5269–5274). The foregoing data establish that the γ-cleavage product of APP forms a complex with Fe65 that transactivates a heterologous promoter, suggesting that the APP/Fe65 complex functions as a transcriptional activator.

To investigate how the APP/Fe65 complex activates transcription, a series of Fe65 deletion mutants were constructed and their ability to stimulate transactivation was determined as described in Example 1. Both APP-Gal4 and APP-LexA were used to ensure that the effects observed were not peculiar to a particular DNA-binding protein (FIG. 5). The WW-domain and both PTB-domains of Fe65 were found to be essential for activating transcription. By contrast, deletion of the N-terminal third of Fe65 with the acidic region suspected of activating transcription had no effect on transactivation (FIGS. 5A and 5B). The results indicate that in addition to the binding of the second PTB domain of Fe65 to the cytoplasmic tail of APP, the WW-domain and the first PTB domain also interact with target molecules in order for Fe65 to stimulate transcription.

The Fe65 deletion mutants suggest that Fe65 is a true adaptor protein in transcriptional regulation. To exclude possible artifacts induced by the deletions, immunoblotting was performed to confirm that all of the transfected proteins were stably expressed, and not prematurely degraded. Immunoprecipitations from COS cells which co-express wild type or mutant Fe65 and APP-Gal4 showed that deletion of the first PTB-domain in Fe65 does not impair its ability to bind to the cytoplasmic tail of APP as long as that tail contains a wild type NPTY sequence (FIGS. 5C and 5D). Finally, point mutations in the WW-domain were used instead of a large deletion to assess the need for the WW domain in the stimulation of transactivation. Substitution of one of the conserved tryptophan residues of the WW-domain had no effect, while replacement of the central YYW motif with alanine residues abolished the Fe65-dependent stimulation of transcription (FIGS. 5A and 5B). Again, immunoblotting confirmed that all mutants were stably expressed, and none of the Fe65 proteins influenced basal transcription from the co-transfected control plasmids. Together these experiments show that all three canonical domains of Fe65 are required to activate transcription in a complex with the cytoplasmic tail of APP, establishing that Fe65 is a genuine adaptor protein which links multiple components into a single active complex.

EXAMPLE 7

Fe65 binds to the histone acetyl transferase tip60. As an adaptor protein, Fe65 presumably directly or indirectly interacts with transcription factors when it activates transcription. A candidate for such a binding protein is the transcription factor LBP/CP2/LSF which interacts with the first PTB-domain of Fe65 (Duilio et al. (1991) Nucleic Acids Res. 19, 5269–5274). However, only a weak interaction between LBP/CP2/LSF and Fe65 was observed in quantitative yeast two-hybrid assays, and no change in the amount of transactivation was detected when LBP/CP2/LSF was co-transfected with Fe65 and APP-Gal4. Other Fe65-interacting proteins were searched for using yeast two-hybrid screens as described in Example 1. A single prey clone that strongly bound to the first PTB-domain of Fe65, and that contains almost the entire coding sequence for Tip60, was identified. Tip60 is a histone acetyl transferase that is expressed in two alternatively spliced forms (Tip60α and β), interacts with multiple transcription factors, and is part of a large complex in the nucleus (Kamine et al. (1996) Virology 216, 357–366). Quantitative yeast two-hybrid assays, GST-pulldown studies, and co-immunoprecipitation experiments confirmed a strong interaction of Fe65 with both the partial rat Tip60β obtained in the yeast two-hybrid screens, and with full-length human Tip60β (FIGS. 6A and 6B). Furthermore, immunofluorescence analyses of transfected cells showed that Fe65 and Tip60β colocalize in the nucleus in a speckled pattern, suggesting that they function as a complex (FIGS. 6C–6F).

PTB-domains usually bind to NPxY target sequences, although variant binding sequences have also been observed (Zwahlen et al. (2000) EMBO J. 19, 15005–15015). In a search for a possible PTB-domain target sequence in Tip60, a single motif was detected that is remotely similar to the NPxY sequences (NKSY; SEQ ID NO:15; residues 257–260). Mapping of the NKSY sequence onto the three-dimensional structure of Esa1, a yeast histon acetyl-transferase whose three-dimensional structure has been solved (Yan et al. (2000) *Mol. Cell* 6, 1195–1205), suggests that the NKSY motif in Tip60 is located on a surface loop of a conserved domain, and thus accessible for a binding partner. To test if the Fe65 PTB1-domain binds to this site, the Tip60 NKSY sequence was mutated into NASA, and the ability of mutant Tip60 to bind to Fe65 was tested. No binding was observed for the mutant as measured either by quantitative yeast two-hybrid assays or GST-pulldowns (FIGS. 6A and 6B), suggesting that the first PTB-domain of Fe65 binds to the NKSY sequence in Tip60.

EXAMPLE 8

Figure 7A:
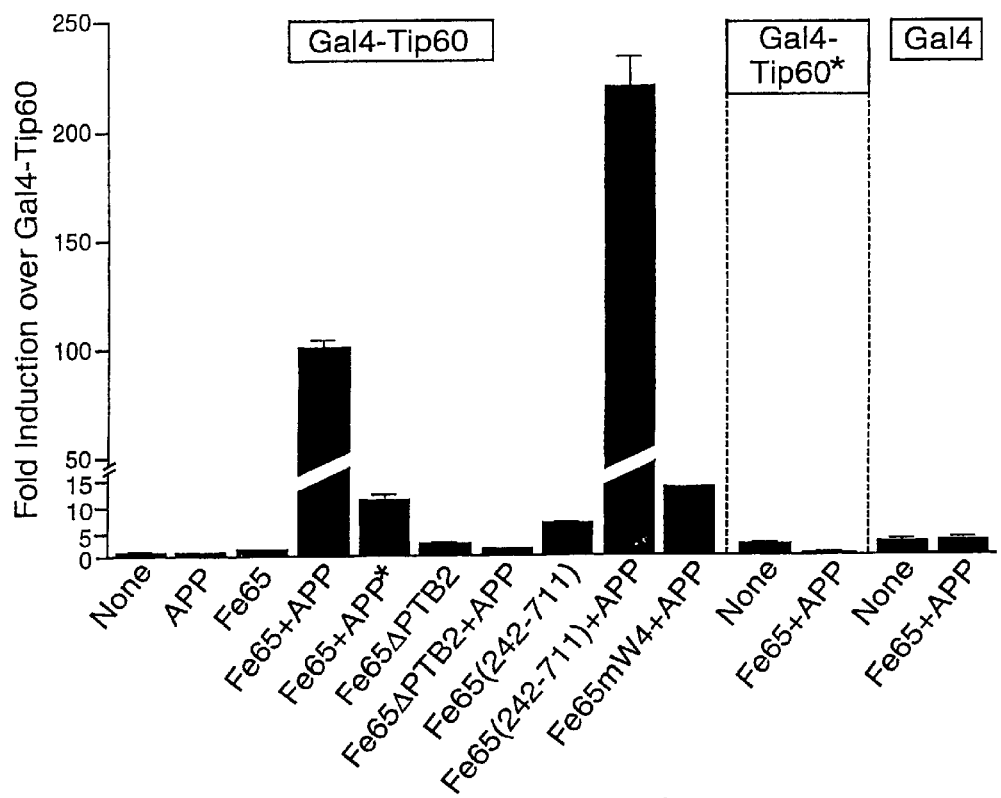
FIG. 7A shows the results of transactivation of Gal4-Tip60 in COS cells co-transfected with full length or mutant Fe65 proteins and/or wild-type or mutant APP proteins.
Figure 7B:
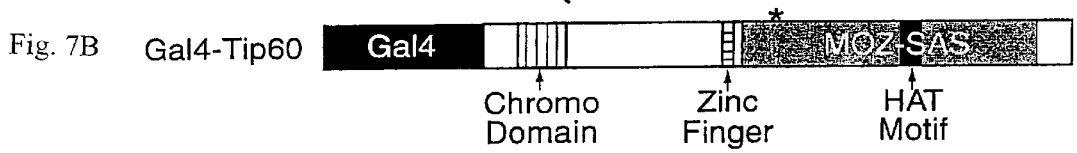
FIG. 7B shows the domain structure of Gal4-Tip60.

Binding of the APP/Fe65 complex to tip60 mediates transactivation. To test if Fe65 enhances transactivation by binding to the Tip60 complex, a Gal4-Tip60 fusion protein was constructed, and the effects of Fe65 and APP on Gal4-dependent transactivation mediated by the Gal4-Tip60 fusion protein were examined (FIG. 7). Gal4-Tip60 alone was unable to support significant Gal4-dependent transcription (no activation over Gal4 alone). Co-expression of either Fe65 or APP individually with Gal4-Tip60 did not enhance transactivation. However, when Gal4-Tip60 was co-expressed with both Fe65 and APP, transactivation was stimulated dramatically (~100 fold; FIG. 7). Mutant APP that is unable to bind to Fe65 (APP*) was largely inactive (~10 fold enhancement of transactivation). Furthermore, no potentiation of transactivation was observed when Fe65 and APP were co-expressed with mutant Gal4-Tip60 (Gal4-Tip60*) that is unable to bind to Fe65, or with Gal4 only. Together these data show that the cytoplasmic tail of APP has a direct active role in stimulating transactivation, and that it collaborates with Fe65 in enhancing transcription by Gal4-Tip60.

In experiments described above (FIG. 5), it was found that all three canonical Fe65 domains (the WW domain and the two PTB domains) are required for Fe65 to potentiate transactivation by Gal4- and LexA-APP proteins. In order to test if the same applies for the Fe65- and APP-dependent transactivation by Gal4-Tip60, a series of Fe65 mutants was examined in this assay (FIG. 7). The N-terminal sequence of Fe65 was not needed for potentiating Gal4-Tip60 dependent transactivation, whereas the second PTB-domain that binds to APP was essential. The WW domain of Fe65 was also found to be indispensable.

Figure 8:
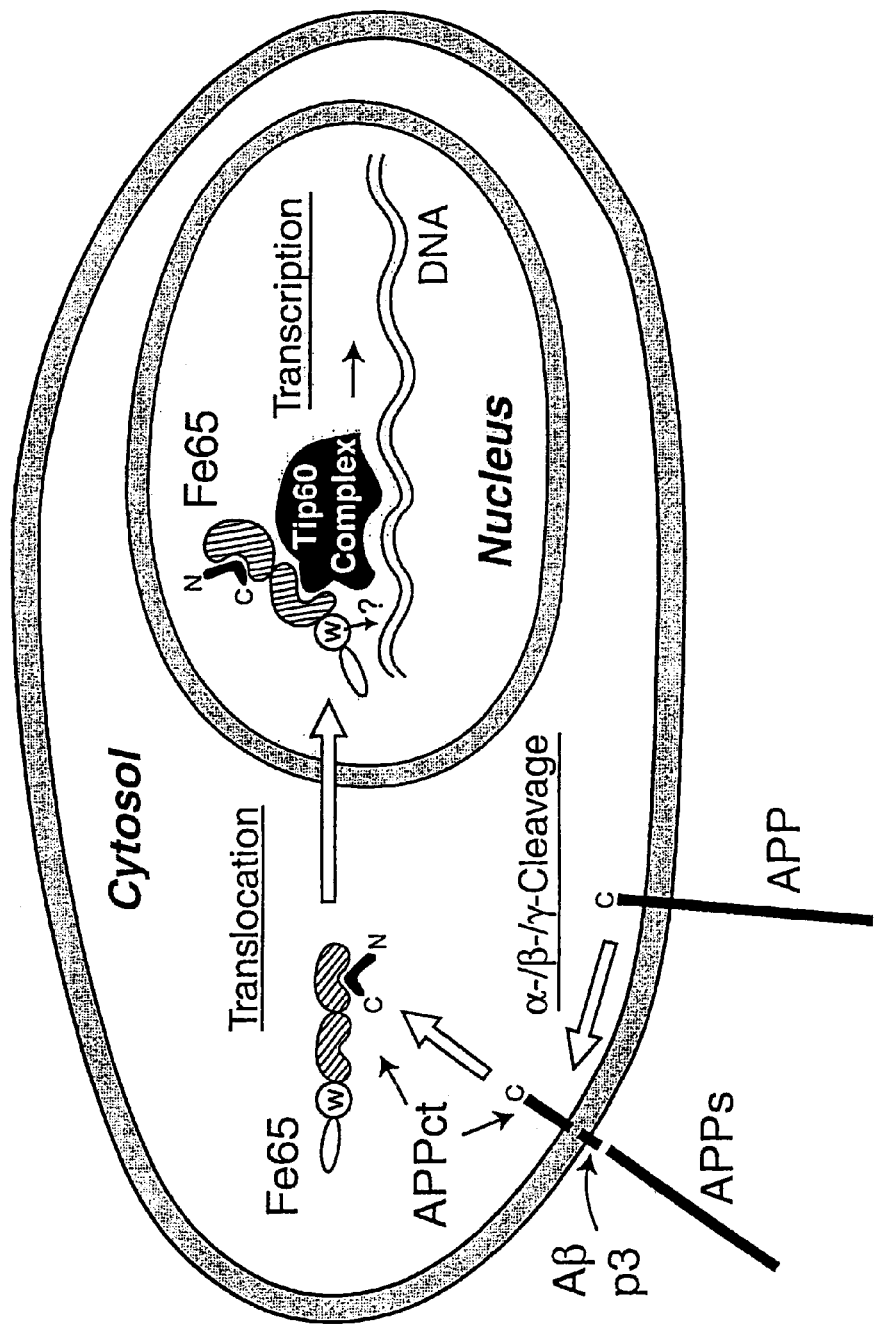
FIG. 8 provides a model for nuclear signaling mediated by the γ-cleavage product of APP in which APP is cleaved by α-, β- and γ-secretases, releasing the 47 residue cytoplasmic tail plus 10–12 hydrophobic residues from the TMR. The cytoplasmic tail complexed with Fe65 is translocated to the nucleus and interacts with Tip60 to regulate transcription.

The foregoing data provide a model for the function of APP and its homologs whereby proteolytic cleavage of APP releases the cytoplasmic tail to activate a nuclear signal in transcription (FIG. 8).

All references cited herein are incorporated herein in their entirety.

We claim:

1. A method of identifying an agent that affects the formation of a functional transcription factor complex between the C-terminal cytoplasmic tail of amyloid-β precursor protein (APP), Fe65 and Tip60 comprising providing a cell containing a modified Tip60 in which Tip60 is fused to a DNA-binding domain, contacting said cell with a candidate agent; and measuring nuclear localization of said C-terminal cytoplasmic tail, wherein an increase or decrease in nuclear localization in the presence of said candidate agent relative to nuclear localization in the absence of said candidate agent is indicative of an agent that affects the formation of a functional transcription factor complex between the C-terminal cytoplasmic tail of APP, Fe65 and Tip60.

2. The method of claim 1 wherein said cell further comprises an indicator gene operably linked to a nucleic acid comprising a binding site for said DNA-binding domain.

3. The method of claim 2 wherein said DNA-binding domain is Gal4 or LexA.

4. The method of claim 2, wherein said transcriptional activator is VP16.

* * * * *